(12) United States Patent
Kilbacak et al.

(10) Patent No.: US 11,931,233 B2
(45) Date of Patent: Mar. 19, 2024

(54) ABSORBENT ARTICLES INCLUDING IMPROVED ELASTIC PANELS

(71) Applicant: The Procter & Gamble Company, Cincinnati, OH (US)

(72) Inventors: Sally Lin Kilbacak, Cincinnati, OH (US); Donald Carroll Roe, West Chester, OH (US); Jeromy Thomas Raycheck, South Lebanon, OH (US); Uwe Schneider, Cincinnati, OH (US); Michael Devin Long, Harrison Township, OH (US); Michael Brian Quade, Blue Ash, OH (US); Jason Edward Naylor, Loveland, OH (US); Jeffry Rosiak, Loveland, OH (US); Stephen Joseph Lange, Cincinnati, OH (US); Urmish Popatlal Dalal, Milford, OH (US); Christopher Krasen, Cincinnati, OH (US); Todd Douglas Lenser, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 105 days.

(21) Appl. No.: 17/307,291

(22) Filed: May 4, 2021

(65) Prior Publication Data
US 2021/0346211 A1    Nov. 11, 2021

Related U.S. Application Data

(60) Provisional application No. 63/143,975, filed on Feb. 1, 2021, provisional application No. 63/020,043, filed on May 5, 2020.

(51) Int. Cl.
*A61F 13/49* (2006.01)
*A61F 13/15* (2006.01)
(Continued)

(52) U.S. Cl.
CPC .. *A61F 13/49011* (2013.01); *A61F 13/15203* (2013.01); *A61F 13/51104* (2013.01);
(Continued)

(58) Field of Classification Search
CPC .......... A61F 13/15203; A61F 13/15699; A61F 13/15707; A61F 13/15731;
(Continued)

(56) References Cited

U.S. PATENT DOCUMENTS 570,255 A    10/1896  Kerner
3,113,225 A  12/1963  Claus
(Continued)

FOREIGN PATENT DOCUMENTS

CN    1144472 A    3/1997
CN    1224606 A    8/1999
(Continued)

OTHER PUBLICATIONS

PCT Search Report and Written Opinion for PCT/US2021/030588 dated Aug. 16, 2021, 15 pages.
(Continued)

*Primary Examiner* — Michael A Tolin
(74) *Attorney, Agent, or Firm* — Daniel S. Albrecht; Sarah M. DeCristofaro; Wednesday G. Shipp

(57) ABSTRACT

An absorbent article includes a first waist region, a second waist region, and a crotch region disposed between the first and second waist regions; and a chassis having a topsheet, a backsheet, and an absorbent core positioned between the topsheet and the backsheet. The article also includes a side panel having an ultrasonically bonded, gathered laminate. The laminate has an elastomeric layer and a substrate and is joined to the chassis at a chassis attachment bond and positioned in one of the first or second waist regions. The ultrasonically bonded, gathered laminate also includes an
(Continued)

ear structural feature comprising a surface modification to the substrate and comprising at least one of the following: embossing, apertures, perforations, slits, melted material or coatings, compressed material, secondary bonds that are disposed apart from a chassis attachment bond, plastic deformation, and folds.

10 Claims, 18 Drawing Sheets

(51) Int. Cl.
 *A61F 13/511* (2006.01)
 *B29C 65/08* (2006.01)
 *B32B 37/00* (2006.01)
(52) U.S. Cl.
 CPC .......... *B29C 65/08* (2013.01); *B32B 37/0084* (2013.01); *A61F 2013/15861* (2013.01); *A61F 2013/15869* (2013.01); *B32B 2310/028* (2013.01); *B32B 2555/02* (2013.01)
(58) Field of Classification Search
 CPC .......... A61F 13/49011; A61F 13/49012; A61F 13/49014; A61F 13/49015; A61F 13/493; A61F 13/51104; A61F 13/5638; A61F 13/68; A61F 2013/15861; A61F 2013/15869; A61F 2013/49022; B29C 65/08; B32B 37/0084; B32B 2310/028; B32B 2555/02
 See application file for complete search history.

(56) References Cited

U.S. PATENT DOCUMENTS

| | | |
|---|---|---|
| 3,562,041 A | 2/1971 | Robertson |
| 3,733,238 A | 5/1973 | Long |
| 3,848,594 A | 11/1974 | Buell |
| 3,860,003 A | 1/1975 | Buell |
| 3,881,488 A | 5/1975 | Delanty et al. |
| 4,116,892 A | 9/1978 | Schwarz |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit |
| 4,556,146 A | 12/1985 | Swanson et al. |
| 4,568,344 A | 2/1986 | Suzuki et al. |
| 4,589,876 A | 5/1986 | Van Tilburg |
| 4,610,678 A | 9/1986 | Weisman |
| 4,662,875 A | 5/1987 | Hirotsu |
| 4,673,402 A | 6/1987 | Weisman |
| 4,687,478 A | 8/1987 | Van Tillburg |
| 4,695,278 A | 9/1987 | Lawson |
| 4,704,115 A | 11/1987 | Buell |
| 4,795,454 A | 1/1989 | Dragoo |
| 4,795,510 A | 1/1989 | Wittrock et al. |
| 4,824,498 A | 4/1989 | Goodwin et al. |
| 4,834,735 A | 5/1989 | Alemany |
| 4,834,741 A | 5/1989 | Sabee |
| 4,846,815 A | 7/1989 | Scripps |
| 4,854,984 A | 8/1989 | Ball |
| 4,888,231 A | 12/1989 | Angstadt |
| 4,894,060 A | 1/1990 | Nestegard |
| 4,909,803 A | 3/1990 | Aziz |
| 4,940,464 A | 7/1990 | Van |
| 4,946,527 A | 8/1990 | Battrell |
| 4,950,264 A | 8/1990 | Osborn, III |
| 5,009,653 A | 4/1991 | Osborn, III |
| 5,026,364 A | 6/1991 | Robertson |
| 5,092,861 A | 3/1992 | Nomura |
| 5,110,403 A | 5/1992 | Ehlert |
| 5,143,679 A | 9/1992 | Weber |
| 5,151,092 A | 9/1992 | Buell |
| 5,156,793 A | 10/1992 | Buell |
| 5,167,897 A | 12/1992 | Weber |
| 5,192,606 A | 3/1993 | Proxmire |
| 5,221,274 A | 6/1993 | Buell |
| 5,242,436 A | 9/1993 | Weil |
| 5,246,433 A | 9/1993 | Hasse |
| 5,267,992 A | 12/1993 | Van Tilburg |
| 5,308,345 A | 5/1994 | Herrin |
| 5,360,420 A | 11/1994 | Cook |
| 5,407,507 A | 4/1995 | Ball |
| 5,422,172 A | 6/1995 | Wu |
| 5,518,801 A | 5/1996 | Chappell et al. |
| 5,540,796 A | 7/1996 | Fries |
| 5,562,646 A | 10/1996 | Goldman |
| 5,569,234 A | 10/1996 | Buell |
| 5,571,096 A | 11/1996 | Dobrin |
| 5,575,783 A | 11/1996 | Clear |
| 5,599,335 A | 2/1997 | Goldman |
| 5,628,097 A | 5/1997 | Benson |
| 5,643,588 A | 7/1997 | Roe |
| 5,669,894 A | 9/1997 | Goldman |
| 5,674,216 A | 10/1997 | Buell |
| 5,693,037 A | 12/1997 | Lee et al. |
| 5,700,255 A | 12/1997 | Curro |
| 5,702,551 A | 12/1997 | Huber |
| 5,735,840 A | 4/1998 | Kline |
| 5,827,259 A | 10/1998 | Laux |
| 5,897,545 A | 4/1999 | Kline |
| 5,904,675 A | 5/1999 | Laux |
| 5,916,661 A | 6/1999 | Benson |
| 5,928,212 A | 7/1999 | Kline |
| 5,957,908 A | 9/1999 | Kline |
| 5,961,997 A | 10/1999 | Swinehart |
| 5,968,025 A | 10/1999 | Roe |
| 5,993,433 A | 11/1999 | St. Louis |
| 6,004,893 A | 12/1999 | Van Tilburg |
| 6,010,491 A | 1/2000 | Roe et al. |
| 6,036,796 A | 3/2000 | Halbert |
| 6,051,094 A | 4/2000 | Melbye et al. |
| 6,107,537 A | 8/2000 | Elder |
| 6,107,539 A | 8/2000 | Palumbo |
| 6,118,041 A | 9/2000 | Roe |
| 6,120,487 A | 9/2000 | Ashton |
| 6,120,489 A | 9/2000 | Johnson |
| 6,149,934 A | 11/2000 | Krzysik et al. |
| 6,153,209 A | 11/2000 | Vega |
| 6,156,023 A | 12/2000 | Yoshioka |
| 6,238,683 B1 | 5/2001 | Burnett et al. |
| 6,248,097 B1 | 6/2001 | Beitz et al. |
| 6,248,195 B1 | 6/2001 | Schmitz |
| 6,251,097 B1 | 6/2001 | Kline |
| 6,369,290 B1 | 4/2002 | Glaug |
| 6,409,883 B1 | 6/2002 | Makolin |
| 6,410,129 B2 | 6/2002 | Zhang |
| 6,426,444 B2 | 7/2002 | Roe |
| 6,432,098 B1 | 8/2002 | Kline |
| 6,454,095 B1 | 9/2002 | Brisebois |
| 6,506,185 B1 | 1/2003 | Sauer et al. |
| 6,508,641 B1 | 1/2003 | Kubik |
| 6,545,197 B1 | 4/2003 | Muller |
| 6,568,530 B2 | 5/2003 | Takahashi |
| 6,572,595 B1 | 6/2003 | Klemp |
| 6,586,652 B1 | 7/2003 | Roe |
| 6,601,705 B2 | 8/2003 | Molina |
| 6,617,016 B2 | 9/2003 | Zhang |
| 6,627,787 B1 | 9/2003 | Roe |
| 6,645,330 B2 | 11/2003 | Pargass |
| 6,648,864 B2 | 11/2003 | Ronn |
| 6,669,618 B2 | 12/2003 | Reising |
| 6,699,228 B1 | 3/2004 | Chmielewski et al. |
| 6,790,798 B1 | 9/2004 | Suzuki |
| 6,825,393 B2 | 11/2004 | Roe |
| 6,830,800 B2 | 12/2004 | Curro et al. |
| 6,861,571 B1 | 3/2005 | Roe |
| 7,087,287 B2 | 8/2006 | Curro et al. |
| 7,371,302 B2 | 5/2008 | Miyamoto et al. |
| 7,569,039 B2 | 8/2009 | Matsuda |
| 7,785,309 B2 | 8/2010 | Van et al. |
| 7,803,244 B2 | 9/2010 | Siqueira et al. |

(56) References Cited

U.S. PATENT DOCUMENTS

| | | |
|---|---|---|
| 7,824,594 B2 | 11/2010 | Qureshi |
| 7,896,641 B2 | 3/2011 | Qureshi |
| 8,062,572 B2 | 11/2011 | Qureshi |
| 8,071,990 B2 | 12/2011 | Bogner et al. |
| 8,118,801 B2 | 2/2012 | Macura et al. |
| 8,186,296 B2 | 5/2012 | Brown |
| 8,257,333 B2 | 9/2012 | Hancock-cooke et al. |
| 8,395,012 B2 | 3/2013 | Bacon et al. |
| 8,496,638 B2 | 7/2013 | Lord et al. |
| 8,608,720 B2 | 12/2013 | Erickson et al. |
| 8,662,706 B2 | 3/2014 | Komatsu |
| 8,715,464 B2 | 5/2014 | Young et al. |
| 8,778,127 B2 | 7/2014 | Schneider |
| 8,936,697 B2 | 1/2015 | Scharpf et al. |
| 8,950,912 B2 | 2/2015 | Chen |
| 8,956,493 B2 | 2/2015 | Tenorio et al. |
| 9,005,392 B2 | 4/2015 | Schneider |
| 9,248,054 B2 | 2/2016 | Brown |
| 9,265,672 B2 | 2/2016 | Brown |
| 9,283,124 B2 | 3/2016 | Hashimoto et al. |
| 9,295,590 B2 | 3/2016 | Brown |
| 9,429,304 B2 | 8/2016 | Masuda et al. |
| 9,464,777 B2 | 10/2016 | Boyce |
| 9,468,569 B2 | 10/2016 | Hancock-cooke et al. |
| 9,687,580 B2 | 6/2017 | Schonbeck |
| 9,913,871 B2 | 3/2018 | Ellington et al. |
| 9,962,297 B2 | 5/2018 | Eckstein et al. |
| 10,052,237 B2 | 8/2018 | Galie et al. |
| 10,159,610 B2 | 12/2018 | Barnes |
| 10,470,943 B2 | 11/2019 | Jang |
| 11,096,836 B2 | 8/2021 | Bishop et al. |
| 11,369,526 B2 | 6/2022 | Matsui et al. |
| 11,554,055 B2 | 1/2023 | Bishop et al. |
| 2002/0064639 A1 | 5/2002 | Rearick et al. |
| 2002/0129740 A1 | 9/2002 | Kato et al. |
| 2002/0165170 A1 | 11/2002 | Wilson et al. |
| 2003/0121380 A1 | 7/2003 | Cowell |
| 2003/0154904 A1 | 8/2003 | Klofta et al. |
| 2003/0187414 A1 | 10/2003 | Reiss et al. |
| 2003/0233082 A1 | 12/2003 | Kline |
| 2004/0097895 A1 | 5/2004 | Busam |
| 2004/0122413 A1 | 6/2004 | Roessler |
| 2004/0158212 A1 | 8/2004 | Ponomarenko |
| 2004/0196734 A1 | 10/2004 | Mehta et al. |
| 2005/0096616 A1 | 5/2005 | Arora et al. |
| 2005/0107764 A1 | 5/2005 | Matsuda |
| 2005/0171498 A1 | 8/2005 | Reiss et al. |
| 2005/0217812 A1 | 10/2005 | Stoyanov et al. |
| 2006/0094320 A1 | 5/2006 | Chen et al. |
| 2006/0129115 A1 | 6/2006 | Visscher |
| 2006/0167434 A1 | 7/2006 | Ashton et al. |
| 2006/0196796 A1 | 9/2006 | Motsch et al. |
| 2006/0264862 A1 | 11/2006 | Yoshida et al. |
| 2006/0264863 A1 | 11/2006 | Blyth |
| 2006/0287637 A1 | 12/2006 | Lam |
| 2007/0032772 A1 | 2/2007 | Ehrnsperger |
| 2007/0078427 A1 | 4/2007 | Raycheck |
| 2007/0093769 A1 | 4/2007 | Kline |
| 2007/0149937 A1 | 6/2007 | Reiss et al. |
| 2007/0219521 A1 | 9/2007 | Hird |
| 2007/0287980 A1 | 12/2007 | Kline et al. |
| 2008/0099360 A1 | 5/2008 | Smith |
| 2008/0250681 A1 | 10/2008 | Jackson |
| 2008/0269704 A1 | 10/2008 | Hansson et al. |
| 2009/0149827 A1 | 6/2009 | Mlinar et al. |
| 2009/0155325 A1 | 6/2009 | Magin et al. |
| 2009/0157034 A1 | 6/2009 | Mattingly et al. |
| 2009/0204090 A1 | 8/2009 | Dennis et al. |
| 2009/0294044 A1 | 12/2009 | Gill et al. |
| 2009/0312730 A1 | 12/2009 | Lavon |
| 2010/0181223 A1 | 7/2010 | Warren |
| 2010/0221496 A1 | 9/2010 | De |
| 2010/0230857 A1* | 9/2010 | Muhs ................ B29C 66/91935 264/284 |
| 2010/0305532 A1 | 12/2010 | Ashton et al. |
| 2011/0040273 A1 | 2/2011 | Sablone |
| 2011/0046594 A1 | 2/2011 | Sablone |
| 2011/0073513 A1 | 3/2011 | Weisman et al. |
| 2011/0139657 A1 | 6/2011 | Hird |
| 2011/0139658 A1 | 6/2011 | Hird |
| 2011/0139659 A1 | 6/2011 | Hird |
| 2011/0139662 A1 | 6/2011 | Hird |
| 2011/0152812 A1 | 6/2011 | Hird |
| 2011/0215017 A1 | 9/2011 | Coulter et al. |
| 2011/0315585 A1 | 12/2011 | Meyer et al. |
| 2011/0319849 A1 | 12/2011 | Collias et al. |
| 2012/0061015 A1 | 3/2012 | Lavon |
| 2012/0061016 A1 | 3/2012 | Lavon |
| 2012/0143165 A1 | 6/2012 | Macura |
| 2012/0206265 A1 | 8/2012 | Solazzo et al. |
| 2012/0276341 A1* | 11/2012 | Lake .................. B31F 1/07 425/336 |
| 2012/0277703 A1 | 11/2012 | Rhein |
| 2012/0277713 A1 | 11/2012 | Raycheck |
| 2013/0018339 A1 | 1/2013 | Kaiser et al. |
| 2013/0072887 A1 | 3/2013 | Lavon |
| 2013/0126071 A1 | 5/2013 | Shin et al. |
| 2013/0211356 A1 | 8/2013 | Nishikawa |
| 2013/0255861 A1 | 10/2013 | Schneider |
| 2013/0255862 A1 | 10/2013 | Schneider |
| 2013/0255863 A1 | 10/2013 | Lavon |
| 2013/0255864 A1 | 10/2013 | Schneider |
| 2013/0255865 A1 | 10/2013 | Brown |
| 2013/0274697 A1 | 10/2013 | Godlewski |
| 2013/0306226 A1 | 11/2013 | Zink |
| 2013/0313149 A1 | 11/2013 | Hird et al. |
| 2014/0005621 A1 | 1/2014 | Roe |
| 2014/0039422 A1 | 2/2014 | Scott |
| 2014/0079919 A1 | 3/2014 | Bunnelle |
| 2014/0093697 A1 | 4/2014 | Perry et al. |
| 2014/0148773 A1 | 5/2014 | Brown |
| 2014/0272370 A1 | 9/2014 | Broyles |
| 2014/0276512 A1 | 9/2014 | Cheng et al. |
| 2014/0352090 A1 | 12/2014 | Schuchter |
| 2014/0371700 A1 | 12/2014 | Patel et al. |
| 2015/0283003 A1 | 10/2015 | Rosati |
| 2015/0366724 A1 | 12/2015 | Fukuzawa et al. |
| 2015/0374561 A1 | 12/2015 | Hubbard, Jr. et al. |
| 2016/0101003 A1 | 4/2016 | Jennewein et al. |
| 2016/0206774 A1 | 7/2016 | Hird |
| 2016/0270973 A1 | 9/2016 | Surushe et al. |
| 2016/0270979 A1 | 9/2016 | Raycheck et al. |
| 2016/0270980 A1 | 9/2016 | Raycheck et al. |
| 2016/0350828 A1 | 12/2016 | Schmidt et al. |
| 2017/0000658 A1 | 1/2017 | Chatterjee |
| 2017/0056253 A1 | 3/2017 | Chester et al. |
| 2017/0246052 A1 | 8/2017 | Ludwig |
| 2017/0252229 A1 | 9/2017 | Bonelli |
| 2017/0290712 A1 | 10/2017 | Findley |
| 2017/0313034 A1 | 11/2017 | Takeda et al. |
| 2017/0319399 A1 | 11/2017 | Desai et al. |
| 2017/0333261 A1 | 11/2017 | Chatterjee |
| 2017/0333262 A1 | 11/2017 | Chatterjee et al. |
| 2018/0042777 A1* | 2/2018 | Dalal ................ A61F 13/15203 |
| 2018/0042778 A1 | 2/2018 | Lenser |
| 2018/0042779 A1 | 2/2018 | Lenser et al. |
| 2018/0042780 A1 | 2/2018 | Lenser et al. |
| 2018/0042785 A1 | 2/2018 | Dalal |
| 2018/0042786 A1 | 2/2018 | Mueller et al. |
| 2018/0042787 A1 | 2/2018 | Lenser et al. |
| 2018/0055698 A1 | 3/2018 | Bishop et al. |
| 2018/0140469 A1 | 5/2018 | Kane et al. |
| 2018/0169964 A1 | 6/2018 | Schneider |
| 2018/0250171 A1 | 9/2018 | Bäck et al. |
| 2018/0256419 A1 | 9/2018 | Mcgilloway et al. |
| 2018/0271716 A1 | 9/2018 | Dalal |
| 2018/0360739 A1 | 12/2018 | Lorenz et al. |
| 2018/0369091 A1 | 12/2018 | Avshalomov |
| 2019/0010258 A1 | 1/2019 | Mitchell et al. |
| 2019/0070042 A1 | 3/2019 | Beck |
| 2019/0083325 A1 | 3/2019 | Mccormick |
| 2019/0083331 A1 | 3/2019 | Barnes |
| 2019/0175417 A1 | 6/2019 | Graham |
| 2020/0038256 A1 | 2/2020 | Jang et al. |

(56) References Cited

U.S. PATENT DOCUMENTS

| | | |
|---|---|---|
| 2020/0054496 A1 | 2/2020 | Mccormick et al. |
| 2020/0054497 A1 | 2/2020 | Mccormick et al. |
| 2020/0078230 A1 | 3/2020 | Mccormick et al. |
| 2020/0093652 A1 | 3/2020 | Mccormick et al. |
| 2020/0093653 A1 | 3/2020 | Mccormick et al. |
| 2020/0121519 A1 | 4/2020 | Mccormick et al. |
| 2020/0163812 A1 | 5/2020 | Zuleger et al. |
| 2020/0197560 A1 | 6/2020 | Buchalter |
| 2020/0375807 A1 | 12/2020 | Schneider et al. |
| 2020/0375815 A1 | 12/2020 | Raycheck et al. |
| 2020/0375816 A1 | 12/2020 | Mccormick et al. |
| 2021/0128366 A1 | 5/2021 | Schneider et al. |
| 2021/0128369 A1 | 5/2021 | Raycheck et al. |

FOREIGN PATENT DOCUMENTS

| | | |
|---|---|---|
| CN | 1328438 A | 12/2001 |
| CN | 101327156 A | 12/2008 |
| CN | 101389237 A | 3/2009 |
| CN | 104244881 A | 12/2014 |
| CN | 106038076 A | 10/2016 |
| CN | 106236389 A | 12/2016 |
| CN | 106456410 A | 2/2017 |
| CN | 107405227 A | 11/2017 |
| CN | 107809989 A | 3/2018 |
| CN | 107820419 A | 3/2018 |
| CN | 109069313 A | 12/2018 |
| CN | 109069315 A | 12/2018 |
| CN | 109475452 A | 3/2019 |
| CN | 109843242 A | 6/2019 |
| CN | 114025727 A | 2/2022 |
| EP | 2260813 B1 | 7/2015 |
| JP | 2002232009 A | 8/2002 |
| JP | 2002541918 A | 12/2002 |
| JP | 2008074327 A | 4/2008 |
| JP | 2008113684 A | 5/2008 |
| JP | 2008113685 A | 5/2008 |
| JP | 2010269029 A | 12/2010 |
| JP | 2011062226 A | 3/2011 |
| JP | 2012243462 A | 12/2012 |
| JP | 2013164937 A | 8/2013 |
| JP | 2013168434 A | 8/2013 |
| JP | 2013180171 A | 9/2013 |
| JP | 2016112341 A | 6/2016 |
| JP | 2016182169 A | 10/2016 |
| JP | 2017060635 A | 3/2017 |
| RU | 24771 U1 | 8/2002 |
| WO | 9511650 A1 | 5/1995 |
| WO | 9524173 A2 | 9/1995 |
| WO | 2007106929 A1 | 9/2007 |
| WO | 2009012284 A1 | 1/2009 |
| WO | 2013002691 A1 | 1/2013 |
| WO | 2014103464 A1 | 7/2014 |
| WO | 2016023016 A1 | 2/2016 |
| WO | 2017118612 A1 | 7/2017 |
| WO | 2017124092 A1 | 7/2017 |
| WO | 2020004476 A1 | 1/2020 |
| WO | 2020004499 A1 | 1/2020 |
| WO | 2020115916 A1 | 6/2020 |
| WO | 2020116554 A1 | 6/2020 |
| WO | 2020116592 A1 | 6/2020 |
| WO | 2020116595 A1 | 6/2020 |

OTHER PUBLICATIONS

All Office Actions; U.S. Appl. No. 17/242,376, filed on Apr. 28, 2021.

U.S. Unpublished U.S. Appl. No. 17/242,376, filed Apr. 28, 2021, to first inventor Sally Lin Kilbacak et al.

"Surround." Merriam-Webster.com Dictionary, Merriam-Webster, https://www.merriam-webster.com/dictionary/surround. Accessed Jun. 15, 2021, 8 Pages.

Epsilon, Water Soluble Dyes/Solvent Green 7 and Corresponding Material Safety Data Sheet, Jul. 15, 2013, 5 pages.

* cited by examiner

ABSORBENT ARTICLES INCLUDING IMPROVED ELASTIC PANELS

FIELD OF THE INVENTION

The present disclosure relates to absorbent articles including elastic panels, and more particularly, to elastic panels having structural features and method for making the same.

BACKGROUND OF THE INVENTION

It has long been known that absorbent articles (e.g., diapers) offer the benefit of receiving and containing urine and/or other bodily exudates. To effectively contain bodily exudates, the article should provide a snug fit around the waist and legs of a wearer.

Some absorbent articles, such as diapers, have components that include elastic parts, such as for example, side panels (i.e., ears) and waistbands. These elastic panels permit a component of an article to closely and comfortably contact the wearer. In various configurations, the panels are laminates which include an elastomeric layer that provides extensibility to the laminate and an outer layer that is less stretchable but suitable for providing durability and desirable tactile properties. The panel may be in the form a gathered laminate, wherein the outer layer forms rugosities when the elastic layer is relaxed. Said gathered laminates may be formed by extending the elastic layer material to a greater extent than the outer material at the time of lamination. Alternatively, the outer layer material may be corrugated and the elastic material may be in its relaxed state at the time of lamination. In either scenario, following lamination, the outer layer gathers or bunches and forms rugosities when the laminate is in a relaxed state. In other configurations, elastic panels may be formed through mechanical activations.

In some configurations, it may be desirable to provide an elastic panel with different zones of performance characteristics, and/or to provide different elastic panels with different characteristics. Indeed, different contraction properties may be desired between, for example, a front waistband and a rear waistband, even when made on the same web. Likewise, it may be desirable to impart enhanced properties to a laminate, versus those properties provided through mere lamination of the precursor webs. Such enhanced properties may include breathability, softness, strength, thickness, uniformity in rugosities, modulus, aesthetic enhancements, tear resistance, combinations of any of the foregoing and/or zones having differing values of any of the foregoing features. It may also be desirable to match properties from one elastic panel to another even where precursor webs may differ.

Therefore, it would be beneficial to provide absorbent articles with elastic panels having enhanced properties and/or structural modifications. It would also be beneficial to impart such properties/modifications online with the lamination process and/or during the absorbent assembly process. It would also be desirable to provide such features in an efficient and/or low cost manner.

SUMMARY OF THE INVENTION

The present invention comprises the features of the independent claims herein. An absorbent article comprises a first waist region, a second waist region, and a crotch region disposed between the first and second waist regions; and a chassis comprising a topsheet, a backsheet, and an absorbent core positioned between the topsheet and the backsheet. The absorbent article further comprises a side panel comprising an ultrasonically bonded, gathered laminate. The ultrasonically bonded, gathered laminate comprises an elastomeric layer and a substrate. The side panel is joined to the chassis at a chassis attachment bond and is positioned in one of the first or second waist regions. The ultrasonically bonded, gathered laminate comprises an ear structural feature comprising a surface modification to the substrate and comprising at least one of the following: embossing, cuts, melted material or coatings, compressed material, secondary bonds that are disposed apart from the chassis attachment bond, plastic deformation, and folds.

A method of forming a side panel for an absorbent article comprises the steps of:
  providing a first substrate and a second substrate, each defining a width in a cross direction;
  creating a morphological difference in the first substrate to form a modified substrate;
  providing an elastomeric material comprising a first edge region and a second edge region separated from the first edge region in the cross direction by a central region;
  stretching the central region of the elastomeric material in the cross direction;
  positioning the stretched central region of elastomeric material between the modified substrate and second substrate; and
  forming an elastic laminate by ultrasonically bonding the modified substrate together with the stretched central region and the second substrate.

A method of forming a side panel for an absorbent article; the method comprising steps of:
  providing a first substrate and a second substrate, each defining a width in a cross direction;
  providing an elastomeric material comprising a first edge region and a second edge region separated from the first edge region in the cross direction by a central region;
  stretching the central region of the elastomeric material in the cross direction;
  positioning the stretched central region of elastomeric material between the first and second substrates;
  forming an elastic laminate by ultrasonically bonding the first substrate together with the stretched central region and the second substrate; and
  creating a morphological difference in a first region of the laminate but not in a second region of the laminate.

DETAILED DESCRIPTION OF THE INVENTION

Figure 1A:
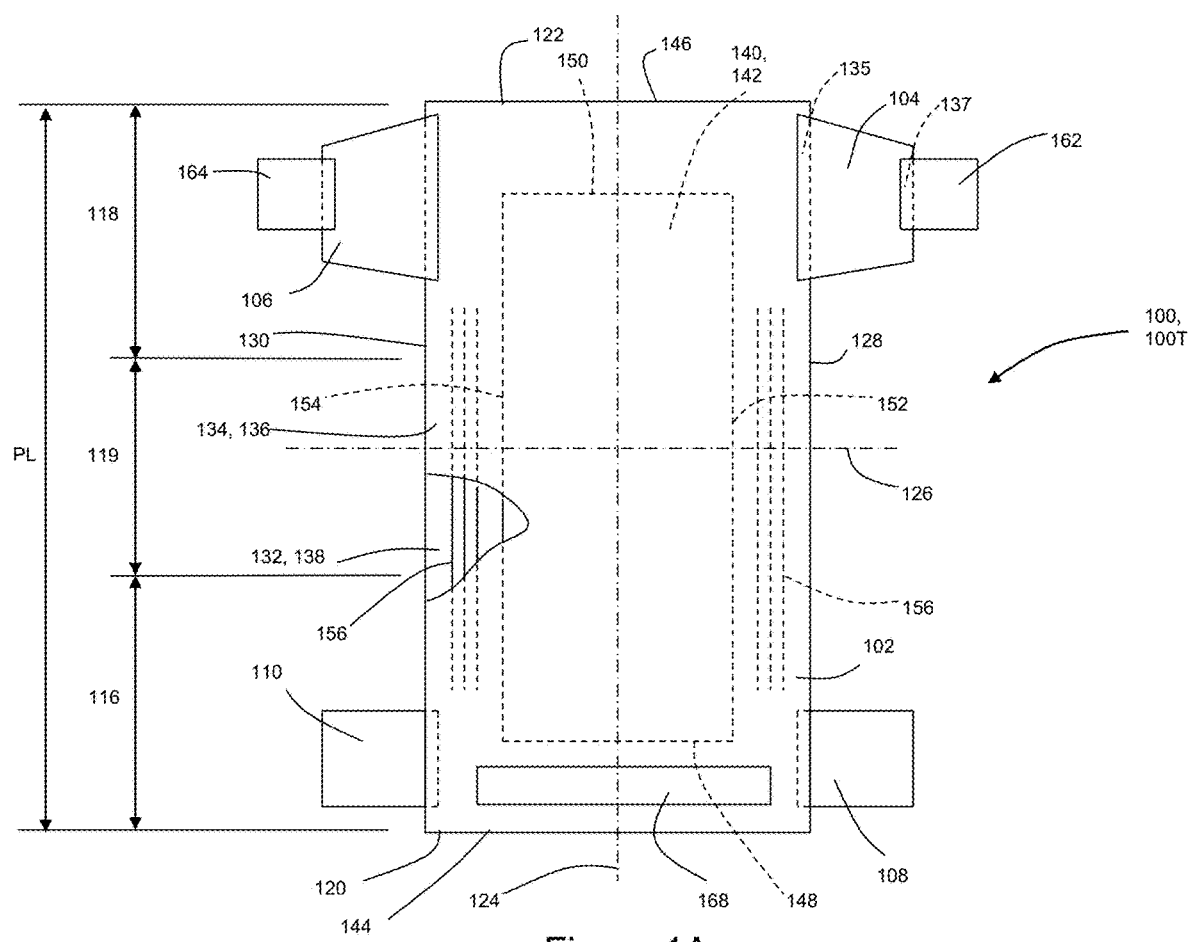
FIG. 1A is a partially cut away plan view of an absorbent article in the form of a taped diaper that may include one or more substrates assembled in accordance with the present disclosure with the portion of the diaper that faces away from a wearer oriented towards the viewer.

The following term explanations may be useful in understanding the present disclosure:

"Absorbent article" is used herein to refer to consumer products whose primary function is to absorb and retain soils and wastes. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts for diapers with a reusable outer cover, and the like. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. In some embodiments, the elastic material can stretch by at least 50% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. As used herein, a laminate is elastic if at least 20% of the area of the laminate meets the elastic definition herein. In this situation, the percent of area of the laminate is determined when the laminate is in a fully stretched state.

"Extensible" means the ability to stretch or elongate, without rupture or breakage, by at least 50% as per step 5(a) in the Hysteresis Test herein.

"Consolidation," "consolidating," and "consolidated" refers to a material undergoing a reduction in elongation from a first stretched length to a second stretched length that is less than the first stretched length and greater than zero.

"Relaxed state" defines a length of material when not stretched by an applied force.

In the context of the present description, an elongation of 0% refers to a material in relaxed state having a relaxed length of L, and elongation of 150% represents 2.5× the relaxed length, L, of the material. For example, an elastic film having a relaxed length of 100 millimeters would have a length of 250 millimeters at 150% elongation. And an elastic film having a relaxed length of 100 millimeters would have a length of 180 millimeters at 80% elongation.

In the context of the present description, a contraction of 60% represents 0.6× contraction of an initial stretch length, L, of a material. For example, an elastic film having an initial stretch length of 250 millimeters would have a contracted length of 100 millimeters at 60% contraction. And an elastic film having an initial stretch length of 180 millimeters would have a length of 100 millimeters at 44% contraction.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Nonlimiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 30 gsm, 40 gsm, or 65 gsm. Some nonwovens may have basis weight of about 8 gsm to about 65 gsm, or about 10 to about 22 gsm, specifically reciting all 1 gsm increments within the above-recited ranges and all ranges formed therein or thereby.

It is to be appreciated that films having various basis weights can be used in accordance with the methods herein. For example, some films may have a basis weight of at least about 8 gsm, 12 gsm, 16 gsm, 20 gsm, 25 gsm, 30 gsm, 40 gsm, or 60 gsm. Some films may have basis weight of about 5 gsm to about 150 gsm, or about 20 gsm to 60 gsm, specifically reciting all 1 gsm increments within the above-recited ranges and all ranges formed therein or thereby.

It is to be appreciated that elastic materials discussed herein may comprise various materials and/or components. Some elastomeric compositions may comprise thermoplastic elastomers selected from the group consisting of styrenic block copolymers, poly-esters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON (styrenic block copolymer; available from the Kraton Chemical Company, Houston, TX), SEPTON (styrenic block copolymer; available from Kuraray America, Inc., New York, NY), VECTOR (styrenic block copolymer; available from TSRC Dexco Chemical Company, Houston, TX) can be used. Additional commercially available elastomers include ESTANE (polyurethane; available from Lubrizol, Inc, Ohio), PEBAX (polyether block amide; available from Arkema Chemicals, Philadelphia, PA), and HYTREL (polyester; available from DuPont, Wilmington, DE).

Semi-crystalline, or metallocene polyolefins may be used in disposable absorbent products. The polyolefin elastomer materials herein may include, but are not limited to, any polymers or copolymers of polyolefins such as polyethylene and polypropylene. Examples of elastomeric polypropylenes include an elastic random poly(propylene/olefin) copolymer, an isotactic polypropylene containing stereo-irregularity, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and blends or combinations thereof. Some homopolyolefins and random copolymers, as well as blends of such random copolymers, known by tradenames Vistamaxx™ available from ExxonMobil and VERSIFY™ from Dow, tend to show elastic performance. In some embodiments, two or more elastomers may be blended to achieve the desired elastic performance. For example, styrenic block copolymer can be blended with polyolefin based elastomers, or polypropylene based elastomer can be blended with other polyolefin based elastomers.

Components of the disposable absorbent articles (i.e., diaper, disposable pant, adult incontinence article, sanitary napkin, pantiliner, etc.) described in this specification can at least partially be comprised of bio-sourced content as described in US 2007/0219521 A1 Hird et al published on Sep. 20, 2007, US 2011/0139658 A1 Hird et al published on Jun. 16, 2011, US 2011/0139657 A1 Hird et al published on Jun. 16, 2011, US 2011/0152812 A1 Hird et al published on Jun. 23, 2011, US 2011/0139662 A1 Hird et al published on Jun. 16, 2011, and US 2011/0139659 A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases. In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B. In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

"Design element" as used herein means a shape or combination of shapes that visually create a distinct and discrete component, regardless of the size or orientation of the component. A design element may be present in one or more patterns. A design element may be present one or more times within one pattern. In one nonlimiting example, the same design element is present twice in one pattern—the second instance of the design element is smaller than the first instance. One of skill in the art will recognize that alternative arrangements are also possible. Design elements may comprise insignia. Design elements and/or combinations of design elements may comprise letters, words and/or graphics such as flowers, butterflies, hearts, character representations and the like. Design elements may be formed from bonds, including the shape of one or more bond(s). Design elements and/or combinations of design elements may comprise instructional indicia providing guidance or instruction to the caregiver relative to placement and/or fit of the article about the wearer.

"Pattern" as used herein means a decorative or distinctive design, not necessarily repeating or imitative, including but not limited to the following: clustered, geometric, spotted, helical, swirl, arrayed, textured, spiral, cycle, contoured, laced, tessellated, starburst, lobed, blocks, pleated, concave, convex, braided, tapered, and combinations thereof. In some embodiments, the pattern includes one or more repeating design elements.

"Insignia" as used herein means objects, character representations, words, colors, shapes or other indicia that can be used to distinguish, identify or represent the manufacturer, retailer, distributor or brand of a product, including but not limited to trademarks, logos, emblems, symbols, designs, figures, fonts, lettering, crests or similar identifying marks.

"Mechanical activation" is the mechanical deformation of a plastically extensible material that results in permanent elongation of the extensible material, or a portion of the extensible material, in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension. A material can be mechanically activated by being passed under tension between the surfaces of a pair of stretching members having intermeshing features. One activation example is ring-rolling. Exemplary methods are mechanical activation are disclosed in for example in U.S. Pat. Pub. No. 2013/0082418, U.S. Pat. Nos. 5,167,897 and 5,993,432. "Pre-activated" refers to a material that has been subjected to activation prior to lamination to another material.

Figure 1B:
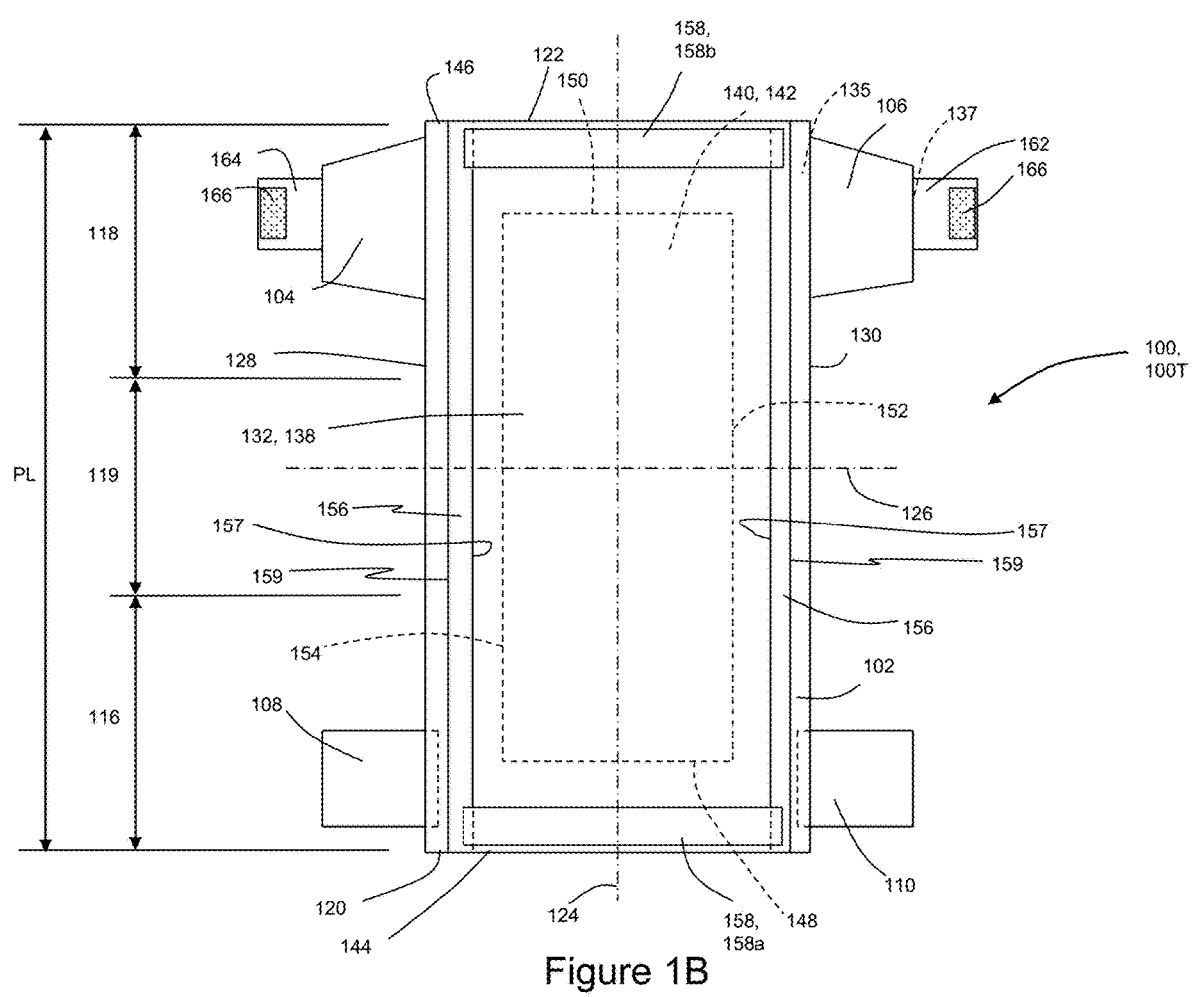
FIG. 1B is a plan view of the absorbent article of FIG. 1A that may include one or more substrates assembled in accordance with the present disclosure with the portion of the diaper that faces toward a wearer oriented towards the viewer.

Aspects of the present disclosure relate to absorbent articles having elastic panels with structural features and/or incorporating precursor materials that have been modified to enhance functionality and desirable properties of the elastic panel and article as a whole. The absorbent articles may be disposable in various embodiments. FIGS. 1A and 1B show an example of an absorbent article 100 that may be assembled in accordance with the present disclosure. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes an absorbent chassis 102, first and second rear side panels 104 and 106; and first and second front side panels 108 and 110.

As shown in FIGS. 1A and 1B, the absorbent article 100 and the chassis 102 each include a first waist region 116, a second waist region 118, and a crotch region 119 disposed intermediate the first and second waist regions. The first waist region 116 may be configured as a front waist region, and the second waist region 118 may be configured as a back waist region. In some embodiments, the length of each of the front waist region, back waist region, and crotch region may be ⅓ of the length of the absorbent article 100. The absorbent article 100 may also include a laterally extending first waist edge 120 in the first waist region 116, wherein the first waist edge 120 may be configured as a front waist edge. In addition, the absorbent article 100 may include a laterally extending second waist edge 122 in the second waist region 118, wherein the second waist edge 122 may be configured as a back waist edge. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the absorbent article 100 includes an inner, wearer facing surface 132, and an outer, garment facing surface 134. As such, it is also to be appreciated that the various components of the absorbent article described below may each include inner, wearer facing surfaces 132, and an outer, garment facing surfaces 134. The chassis 102 may include a backsheet 136 and a topsheet 138. The chassis 102 may also include an absorbent assembly 140, including an absorbent core 142, disposed between a portion of the topsheet 138 and the backsheet 136.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the absorbent article 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118. However, for better fit, longitudinal edges 112 may be curved or angled to produce, for example, an "hourglass" shape article.

It is to also be appreciated that a portion or the whole of the absorbent article 100 may also be made laterally extensible. The extensibility may help allow the absorbent article 100 to conform to the body of a wearer during movement by the wearer. The extensibility may also help, for example, the user of the absorbent article 100, including a chassis 102 having a particular size before extension, to extend the front waist region 116, the back waist region 118, or both waist regions of the absorbent article 100 and/or chassis 102 to provide additional body coverage for wearers of differing size, i.e., to tailor the absorbent article to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the absorbent article 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the absorbent article 100, such as bedsheets, pajamas and undergarments. The backsheet 136 may also comprise a woven or nonwoven material (e.g., a hydroentangled nonwoven material), polymeric films such as thermoplastic films of polyethylene or polypropylene, and/or a multi-layer or composite materials comprising a film and a nonwoven material (e.g., having an inner film layer and an outer nonwoven layer). The backsheet 136 may also comprise an elastomeric film. An example backsheet 136 may be a polyethylene film having a thickness of from about 0.012 mm (0.5 mils) to about 0.051 mm (2.0 mils). The backsheet 136 may comprise a bond pattern, apertures, and/or three-dimensional features and may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the absorbent article 100.

Also described above, the absorbent article 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, bicomponent or otherwise processed as is known in the art. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

As mentioned above, the chassis 102 may also include an absorbent assembly 140. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the absorbent article.

An absorbent core may comprise a wide variety of liquid-absorbent materials. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). In some embodiments, the absorbent core may comprise one or more channels, wherein said channels are substantially free of absorbent material. Exemplary absorbent structures are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 15/232,901.

One or more masking layers or materials may be provided in the absorbent article. A masking layer may be a layer that provides a cushiony feel when the absorbent article is touched from the garment-facing surface or the wearer-facing surface. The masking layer may "mask" a grainy feel potentially caused by the absorbent material, such as superabsorbent polymers. The masking layer may "mask" bodily exudates from being visible when viewing the wearer-facing surface or the garment-facing surface of the absorbent article. The masking layer may have a basis weight in the range of about 15 gsm to about 50 gsm or about 15 gsm to about 40 gsm. The masking layer may comprise one or more nonwoven materials (e.g., a hydroentangled nonwoven material), foams, pulp layers, and/or other suitable materials. The masking layer may be the outer cover material of the backsheet. The masking layer may be the layer forming the garment-facing side or the wearer-facing side of the core. The masking layer may be a separate material positioned intermediate the garment-facing side of the core and the liquid impermeable backsheet.

Taped diapers may be manufactured and provided to consumers in a configuration wherein the front waist region and the back waist region are not fastened, pre-fastened, or connected to each other as packaged, prior to being applied to the wearer. For example, the taped diaper 100T may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The absorbent article 100 may also include various configurations of fastening elements to enable fastening of the front waist region 116 and the back waist region 118 together to form a closed waist circumference and leg openings once the absorbent article is positioned on a wearer. For example, as shown in FIGS. 1A and 1B, the absorbent article 100 may include first and second fastening members 162, 164, also referred to as tabs, connected with the first and second rear side panels 104, 106, respectively. The absorbent article may also include first and second front side panels 108, 110, that may or may not include fastening members.

The side panels may be integral with the chassis 102 or discrete elements joined to the chassis 102 at a chassis attachment bond 135, which joins one or more layers of the side panel to the chassis. At least a portion of the side panel may comprise printing and/or may comprise a tinted substrate.

Figure 2:
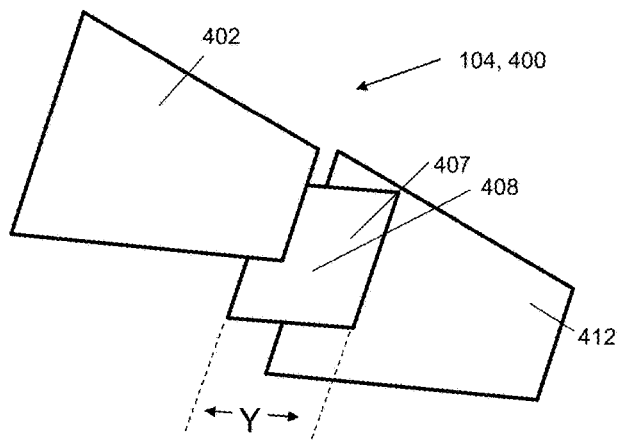
FIG. 2 is an exploded perspective view of an exemplary side panel.

Turning to FIG. 2, a side panel may comprise a laminate 400 having a first substrate 402 and an elastomeric layer 407. The laminate may comprise a second substrate 412, and the elastomeric layer 407 may be sandwiched between the first and second substrates. The first and/or second substrate may comprise a nonwoven. The first and second substrates may be the same or may be different. Where the laminate 400 comprises more than one nonwoven, the nonwovens may comprise the same basis weight or different basis weights. Likewise, the nonwovens may comprise the same layer configuration (e.g., SSS) or different layer configurations (e.g., SMS). Additional layers may be included (e.g., additional nonwovens, inelastic materials, elastic or extensible materials, etc.). The laminate may be extensible. In various configurations, the laminate is elastic.

The elastomeric layer 407 comprises one or more elastomeric materials which provide elasticity to at least a portion of the layer 407. Nonlimiting examples of elastomeric materials include film 408 (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, and the like.

Figure 2A:
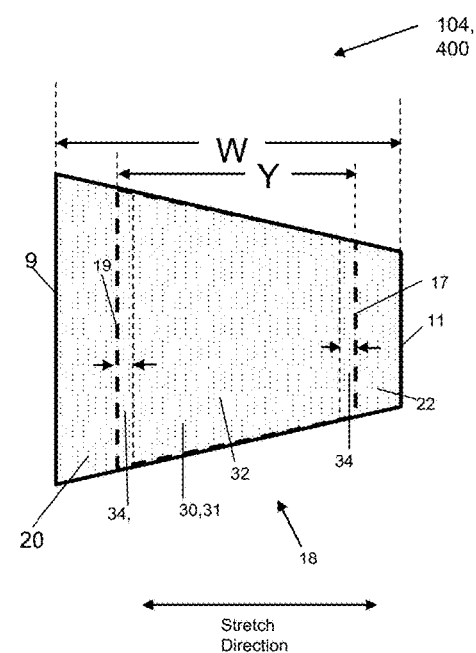
FIG. 2A is a plan view of the exemplary side panel of FIG. 2.

As shown in FIGS. 2-2A, the elastomeric layer may be shorter in one or more dimensions of the laminate than the laminate itself. For example, the elastomeric layer may comprise a maximum dimension, Y, in the stretch direction and the laminate may comprise a maximum dimension, W, in the stretch direction. These maximum dimensions are measured when the laminate is in the relaxed state. In nonlimiting examples, Y may be less than W, by at least about 10 mm. In certain embodiments, Y is at least about 20% of, or from about 25% to about 100%, or from about 35% to about 85%, or about 80% or less of W, reciting for each range every 5% increment therein. In various embodiments, the stretch direction is the lateral direction. Additionally, or alternatively, the elastomeric layer may have a dimension that is equal to one or more dimensions of the laminate. For example, the elastomeric layer may comprise substantially the same longitudinal length of the laminate throughout the lateral width of the laminate. In some embodiments, the elastomeric layer may have a basis weight of from about 5 to about 150 gsm, or from about 10 to about 100 gsm, or less than about 150 gsm, reciting for each range every 5 gsm increment therein.

Turning to FIG. 2A, the laminate 400 may comprise a primary region 18, defined by the perimeter of the elastomeric material 407, and one or more inelastic regions 20, 22. In some configurations, the primary region 18 comprises an elastic region 32 and one or more unstretched zones 34. In the elastic region, the laminate is elastically extensible. In the unstretched zones, the laminate may not be elastic despite the presence of the elastomeric layer. In some embodiments, the area of the primary region comprises at least about 20% of, or from about 30% to about 100% of, or about 80% or less of the total area of the laminate, reciting for said range every 5% increment therein.

As noted, the laminate may further comprise one or more inelastic regions. In certain embodiments, the laminate 400 comprises a first inelastic region 20, which extends laterally outward from a first laminate edge 9 of the laminate and is adjacent to the primary region 18 at a first elastomeric material edge 17. The ear may further include a second inelastic region 22, which may extend laterally inward from a second laminate edge 11 and may be adjacent to the primary region 18 at a second elastomeric material edge 19. The first and second inelastic regions may be made of the same material(s) or different materials.

Two or more laminate layers may be joined by a plurality of bonds 30, such as ultrasonic bonds 31. Ultrasonically bonded laminate may be formed by any suitable processes, including but not limited to those described in commonly assigned U.S. Patent Publication Nos. 2018/0042778 A1; 2018/0042787 A1; 2018/0042779 A1; and 2018/0042780 A1. The bonds may comprise heat bonds, pressure bonds or combinations thereof. The bonds may be any suitable shape or size. The bonds may be disposed in a pattern 24.

Figure 3:
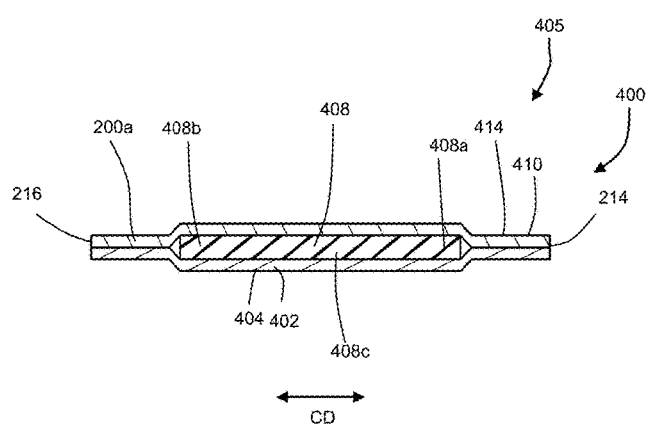
FIG. 3 is a cross sectional view of an exemplary elastic laminate.
Figure 4:
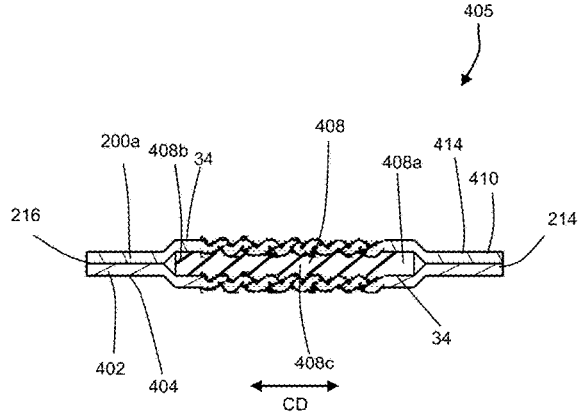
FIG. 4 is a cross-sectional view of the elastic laminate from FIG. 3 in a relaxed, contracted condition.

FIGS. 3 and 4 show a cross sectional views of a laminate 400 that may serve as a side panel; the laminate includes a first substrate 402, a second substrate 410, and an elastic film 408 positioned between the first substrate 402 and the second substrate 410, wherein the first substrate 402 and/or second substrate 410 may be configured as a nonwoven as discussed above. The laminate is shown to be a gathered laminate 405, wherein one of the layers (ideally elastomeric layer) is strained to a greater degree in a stretch direction SD (i.e., the intended direction of stretch in the final product) than a remaining layer during lamination. In this way, the less extensible layer (i.e., the substrates 402, 410) will form gathers when the laminate 400 is in a relaxed state.

In some embodiments, at least a portion of the elastomeric layer is strained while the substrate(s) (e.g., nonwoven(s)) are in a relaxed state during lamination. The elastomeric layer may be stretched one or more directions. Corrugations then form in the substrate layer(s) 402, 410 when the subsequently formed laminate 400 is in a relaxed state. In various configurations, the elastomeric layer is stretched in a direction corresponding with the lateral direction of the article. In other words, when the laminate is joined to the chassis subsequent to lamination, the laminate will be oriented such that the laminate is stretchable in the lateral direction of the article (i.e., the laminate is laterally-extensible). An unstretched zone 34 is formed in a gathered laminate in a portion of the laminate comprising an elastomeric material that was substantially in a relaxed state during lamination. During such lamination, a portion of the elastomeric material is not extended, typically in order to hold the elastomeric layer in position on equipment. In the final laminate, these unextended portions together with the overlapping portions of other laminate layers form the unstretched zones 34.

In some configurations, the elastic film 408 may be bonded together with the first and/or second substrates 402, 410, and the first substrate 402 may be bonded directly to the second substrate 410 in areas of the laminate 400. In some configurations, the first and second substrates 402, 410 may be bonded directly to each other through apertures in the elastic film 408, wherein such apertures may be formed during the bonding process. In some configurations, the elastic film 408 can be involved, or participate, in the bonding between the first and second substrates 402, 410, wherein "involved" can mean that the elastic film 408 can, to some extent, be in intimate contact with, and possibly partially merged with, one or both the first and second substrates 402, 410. The involvement may be due to actual melt bonding about the perimeter of a bond site or may be due to mechanical interaction, such as by entanglement of a fibrous elastic layer between fibrous nonwoven layers also about the perimeter of bond site. which are all incorporated by reference herein.

Figure 2B:
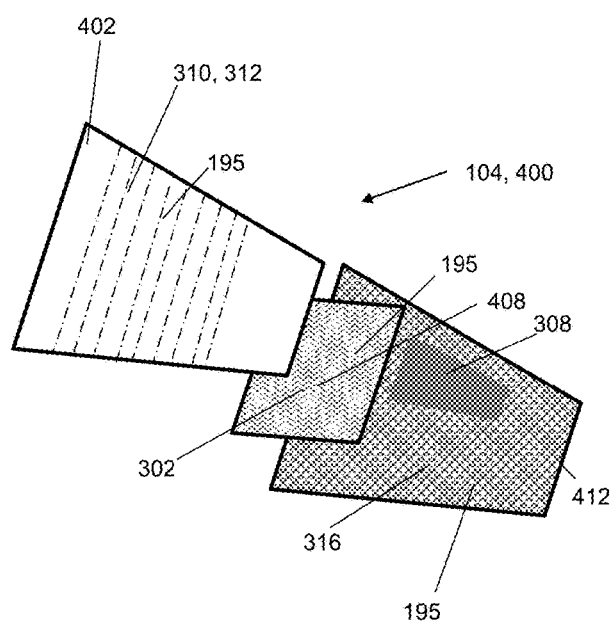
FIG. 2B is an exploded perspective view of the exemplary side panel of FIG. 2 schematically illustrating exemplary surface modifications.
Figure 2C:
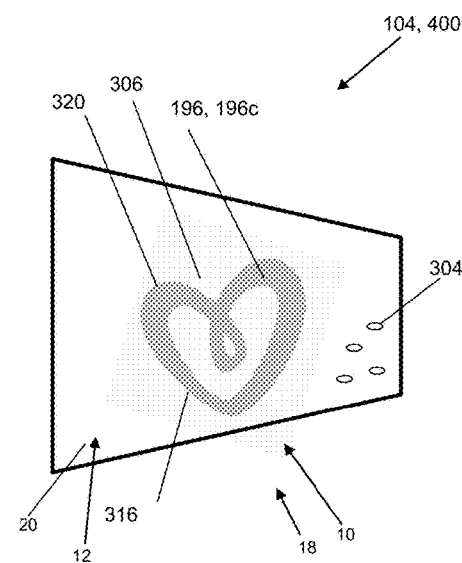
FIG. 2C is a plan view of an exemplary side panel illustrating exemplary structural features according to a nonlimiting embodiment of the present invention.

As shown in FIGS. 2B-2C, the laminate may comprise one or more structural features 196. The structural features are formed through surface modifications 195 on the laminate or layers of the laminate after initial bonding of the layers and/or formed through one or more surface modifications 195 (also referred to as morphological differences or morphological features) of precursor material of one or more individual layers of the laminate prior to lamination. In some embodiments, the structural feature may be disposed in a primary region 18. Structural features may comprise embossing 302, cuts 304 (e.g., apertures, perforations, slits), melted material or coatings 306, compressed material 308, plastic deformation 310 (e.g., activation stripes 312), folds 314, secondary bonds 316 (e.g., adhesive bonds, pressure bonds, thermal bonds, and/or ultrasonic bonds applied after the initial bonding of the laminate) and combinations thereof. Structural features may be disposed throughout the length and/or width of the laminate. Alternatively, structural features may be disposed apart from a chassis attachment bond 135 and/or apart from a fastener attachment bond 137. Structural features may, for example, be disposed a minimum distance of about 5 mm, or about 7 mm or from about 2 mm to about 50 mm from the chassis attachment bond and/or from a fastener attachment bond. Surface modifications may comprise embossing 302, cuts 304 (e.g., apertures, perforations, slits), melted material or coatings 306, compressed material 308, plastic deformation 310 (e.g., activation stripes 312), folds 314, post-formation bonds 316 (e.g., adhesive bonds, pressure bonds, thermal bonds, and/or ultrasonic bonds applied after the substrate is formed) and combinations thereof. Surface modifications are formed after the initial formation of the substrate itself, thereby forming a modified substrate. In other words, thermal bonding fibers to produce a nonwoven is not considered a surface modification. Creating bonds on the nonwoven once it has been formed is considered a surface modification.

It is to be appreciated that certain substrates may be selected for their susceptibility to certain surface modifications and/or techniques, and/or for the properties more likely to be generated from applying a technique or forming a particular modification from a given substrate. By way of nonlimiting example, a carded nonwoven may be selected if mechanically activating the substrate and/or laminate. Lower modulus materials, such as polyethylene-based materials, may be more suitable for modification through laser energy.

Where surface modifications 195 are formed on more than one layer, they may be the same type of modification or different types, the latter being illustrated in FIG. 2B. Additionally, or alternatively, surface modifications 195 on different layers may work together to provide an enhanced property as is discussed more fully below. Surface modifications and structural features are described in more detail below.

Returning to FIGS. 1A and 1B, each side panel 104, 106 and/or fastening member 162 and 164 may form a portion of or may be permanently bonded, adhered or otherwise joined directly or indirectly to the chassis 102 at a chassis attachment bond disposed laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. In some embodiments, the fastening member is joined to the side panel at a fastener attachment bond 137. The fastening member may be joined to the side panel between layers, or joined to the side panel on an exterior surface of the side panel. In one nonlimiting example, the fastening member 162 is ultrasonically bonded to the side panel or chassis. The substrate layer(s) of the side panel may be folded at the fastening attachment bond and/or at the side of the side panel where the fastening member is attached.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macro-fasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846,815; 4,894,060; 4,946,527; 5,151,092; 5,221,274; 5,242,436; 6,251,097; 6,669,618; 6,432,098; U.S. Patent Publication Nos. 2007/0078427 A1 and 2007/0093769 A1; and U.S. patent application Ser. No. 16/685,230, which are all incorporated by reference herein.

As previously mentioned, the fastening members 162 and 164 may be constructed from various materials and may be constructed as a laminate structure. The fastening members 162 and 164 may also be adapted to releasably and/or refastenably engage or connect with another portion of the absorbent article 100. For example, as shown in FIG. 1A, the absorbent article 100 may include a connection zone 168, sometimes referred to as a landing zone, in the first waist region 116. As such, when the taped absorbent article 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the absorbent article. In some embodiments, the connection zone may be integrally formed as part of the backsheet 136 of the absorbent article 100 or may be formed as part of the first and second front panels 108, 110.

With continued reference to FIG. 1B, the absorbent article 100 may also include leg gasketing elements 156. It is to be appreciated that the leg gasketing elements 156 can be and are sometimes also referred to as leg cuffs, leg bands, side flaps, barrier cuffs, elastic cuffs or gasketing cuffs. The leg gasketing elements 156 may be elasticized and may be configured in various ways to help reduce the leakage of body exudates in the leg regions. Example leg gasketing elements 156 may include those described in U.S. Pat. Nos. 3,860,003; 4,909,803; 4,695,278; 4,795,454; 4,704,115; 7,435,243; 8,062,279; 8,939,957; and U.S. Patent Publication No. 2009/0312730 A1, which are all incorporated by reference herein.

As shown in FIG. 1B, the absorbent article 100 may include longitudinally extending and laterally opposing leg gasketing elements 156 that are disposed on the interior surface 132 of the chassis 102 that faces inwardly toward the wearer and contacts the wearer. Each leg gasketing element 156 may have a first side edge 157 and a second side edge 159, wherein the first side edge 157 is positioned laterally inboard of the second side edge 159. The leg gasketing elements 156 may also overlap the absorbent assembly 140, wherein the first side edges 157 extend laterally inward of the respective side edges 152, 154 of the absorbent assembly 140. In some configurations, the leg gasketing elements 156 may not overlap the absorbent assembly 140. It is to be appreciated that the leg gasketing elements 156 may be formed in various ways, such as for example, by folding portions of the chassis 102 laterally inward, i.e., toward the longitudinal axis 124, to form both the respective leg gasketing elements and the side edges 128 and 130 of the chassis 102. In another example, the leg gasketing elements 156 may be formed by attaching an additional layer or layers to the chassis 102 at or adjacent to each of the respective side edges and of the chassis. Each of the leg gasketing elements 156 may be joined to the interior surface 132 of the chassis and/or the absorbent assembly 140 in leg gasketing element attachment zones in the front waist region 116 and in leg gasketing element attachment zones in the back waist region 118. The leg gasketing elements 156 may extend to the same longitudinal extent as the absorbent article 100 or alternatively the leg gasketing elements 156 may have a longitudinal extent that is less than the absorbent article 100. In some configurations, the leg gasketing elements may be configured to define inner cuffs, outer cuffs, or both inner and outer cuffs.

The absorbent article 100 may also include one or more waist panels 158, such as shown in FIG. 1B. The waist panel 158 may provide improved fit and containment and may define a portion or zone of the absorbent article 100 that may elastically expand and contract to dynamically fit a wearer's waist. The absorbent article 100 may also include more than one waist panels 158, for example, having a first panel 158a positioned in the first waist region 116 and second waist panel 158b positioned in the second waist region 118, although other configurations may be constructed with a single waist panel 158. The waist panel 158 may be constructed in a number of different configurations including those described in U.S. Pat. Nos. 4,515,595 and 5,151,092, and U.S. patent application Ser. Nos. 16/864,267; 16/864,292; 62/855,001; 62/930,181; 62/930,198; and 62/930,808, which are all incorporated herein by reference.

It is to be appreciated that the waist panels 158 herein may be configured in various ways and may include one or more elastic materials, such as for example, elastic film and/or strands. For example, the waist panel 158 may be configured as a single layer of elastic film. In some configurations, the waist panel 158 may be configured as a laminate of two more substrates. For example, the waist panel 158 may be configured as an elastic film bonded in between two or more nonwoven substrates and/or may be bonded with one or more nonwoven substrates. For example, the waist panel 158 may be configured as a bi-laminate with an elastic film bonded with a single nonwoven substrate. In another example, the waist panel 158 may be configured as an elastic film bonded between two or more substrates, wherein the substrates may comprise nonwovens. It is also to be appreciated that nonwoven substrates of the waist panel 158 may be of the same or different material and/or basis weights and may be configured as an elastomeric nonwoven or a non-elastic nonwoven. In some configurations, one more nonwoven substrates of the waist panel 158 may be of the same or different material and/or basis weights as one more nonwoven substrates of the topsheet 138, backsheet 136, side panel 104, 106 and/or leg gasketing elements 156.

Waist panels 158 herein may be formed in various ways and may include various components bonded together in various ways and with differing or identical bond patterns. For example, the waist panels 158 herein may comprise a laminate of an elastic film bonded with at least one nonwoven in a stretched state. For example, the waist panel may be in the form of the laminate 400 discussed above and illustrated in FIG. 3 for example. In some configurations, the waist panel may be bonded continuously or discontinuously. In some configurations, the laminate may be bonded with a plurality of individual bond sites that may or may not form a visually discernable pattern.

Components of the waist panel 158 may be bonded together in various ways, such as for example, by adhesive bonds, ultrasonic bonds, pressure bonds, thermal bonds or combinations thereof. In some configurations, components of the waist panel 158 may be mechanically (pressure) bonded with the application of pressure (and optionally heat) in various ways, such as for example, the mechanical bonding devices and methods disclosed in in U.S. Pat. Nos. 4,854,984; 6,248,195; 8,778,127; 9,005,392; 9,962,297; and 10,052,237, which are all incorporated by reference herein. In some configurations, components of the waist panel 158 may be mechanically (pressure) bonded with the use of ultrasonic bonding methods configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. The waist panel 158 may be formed with various types of bond configurations, such as disclosed, for example, in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, In some configurations, the waist panel 158 may be formed as a zero strain stretch laminate that may be connected with the chassis 102 in a stretched state. In some configurations, the zero strain stretch laminate may include at least a layer of nonwoven material and an elastomeric element. The elastomeric element may be attached to the layer of nonwoven material while in a relaxed or substantially relaxed state, and the resulting laminate is made stretchable (or more stretchable over a further range) by subjecting the laminate to an activation process, which elongates the nonwoven layer permanently and elongates the elastomeric element temporarily. In some configurations, the nonwoven layer may be a separate component, in which case the elastomeric element is attached to the nonwoven layer to form the laminate, which is then connected with the chassis 102. In some configurations, the nonwoven layer may be integral with at least a portion of the chassis 102, in which case the elastomeric element may be attached to the nonwoven layer and the nonwoven/elastomeric element laminate is subsequently activated. In some configurations, the waist panel may be an extrusion bonded laminate. If one or more layers of the waist panel 158 are provided separately, the waist panel 158 may be activated either before or after attachment to the chassis 102. Examples of zero strain activation processes are disclosed in U.S. Pat. Nos. 5,167,897 and 5,156,793, which are incorporated by reference herein. In embodiments where the laminate is a zero strain activated laminate, it is to be appreciated that a structural feature may still comprise a plastic deformation in the form of an activation stripe 312, in particular an activation stripe that is formed by a secondary, subsequent activation of the laminate. The secondary activation may, for example, produce activation stripes having a different orientation than the initial activation stripes and/or may provide stretch in a direction different than that imparted during lamination.

The waist panel 158 may be located in various positions relative to the garment facing surfaces 132 and wearer facing surfaces 134 of various absorbent article components. The waist panel 158 may be positioned on the wearer facing surface 132 of the topsheet 138 and/or the wearer facing surfaces of the leg gasketing elements 156. In some configurations, the waist panel 158 may be positioned on the wearer facing surfaces 132 of the topsheet 138 and laterally opposing end regions of the waist panel 158 may be positioned between the leg gasketing elements 156 and the topsheet 138. In some configurations, the waist panel 158 may be positioned between the garment facing surface 132 of the topsheet 138 and the wearer facing surface 132 of the backsheet 136. And in some configurations, the waist panel 158 may be positioned on the garment facing surface 134 of the backsheet 136.

Figure 5:
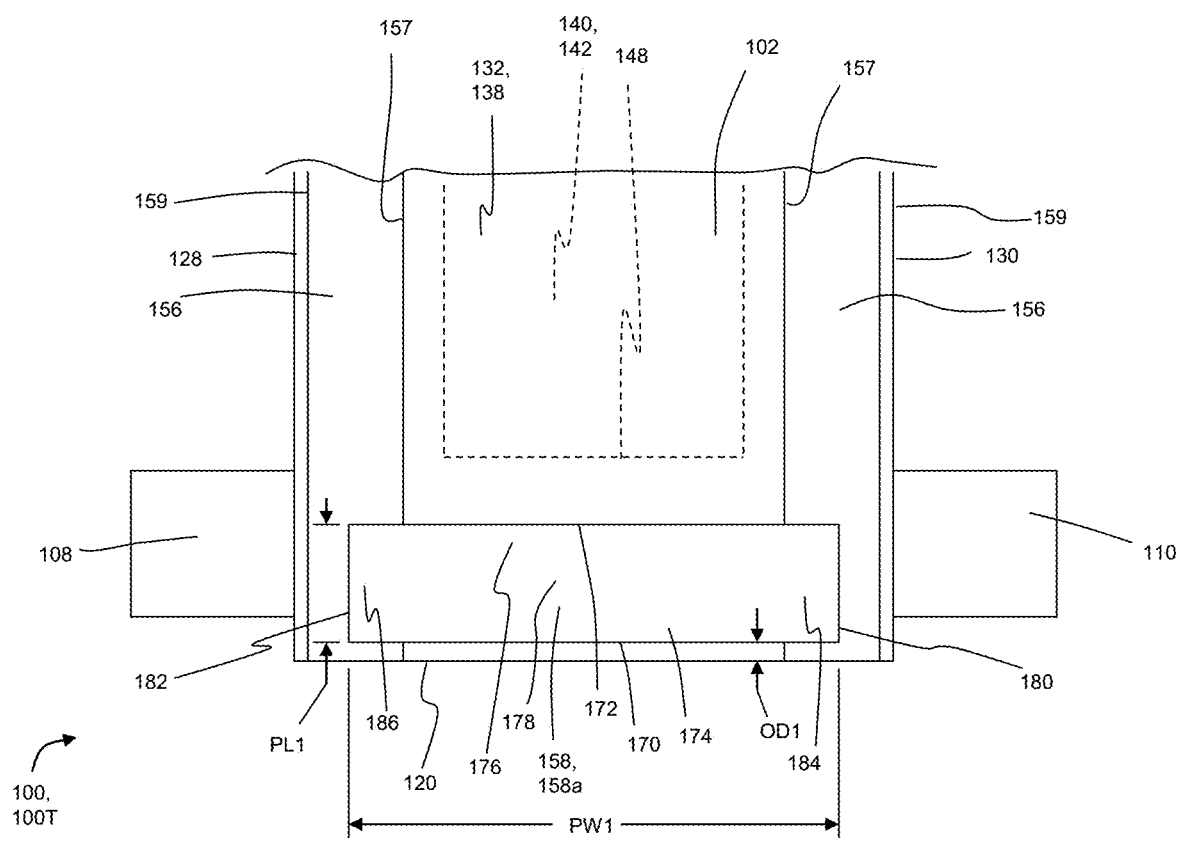
FIG. 5 is a detailed view of a first waist panel with the portion of the diaper that faces toward a wearer oriented towards the viewer.
Figure 6:
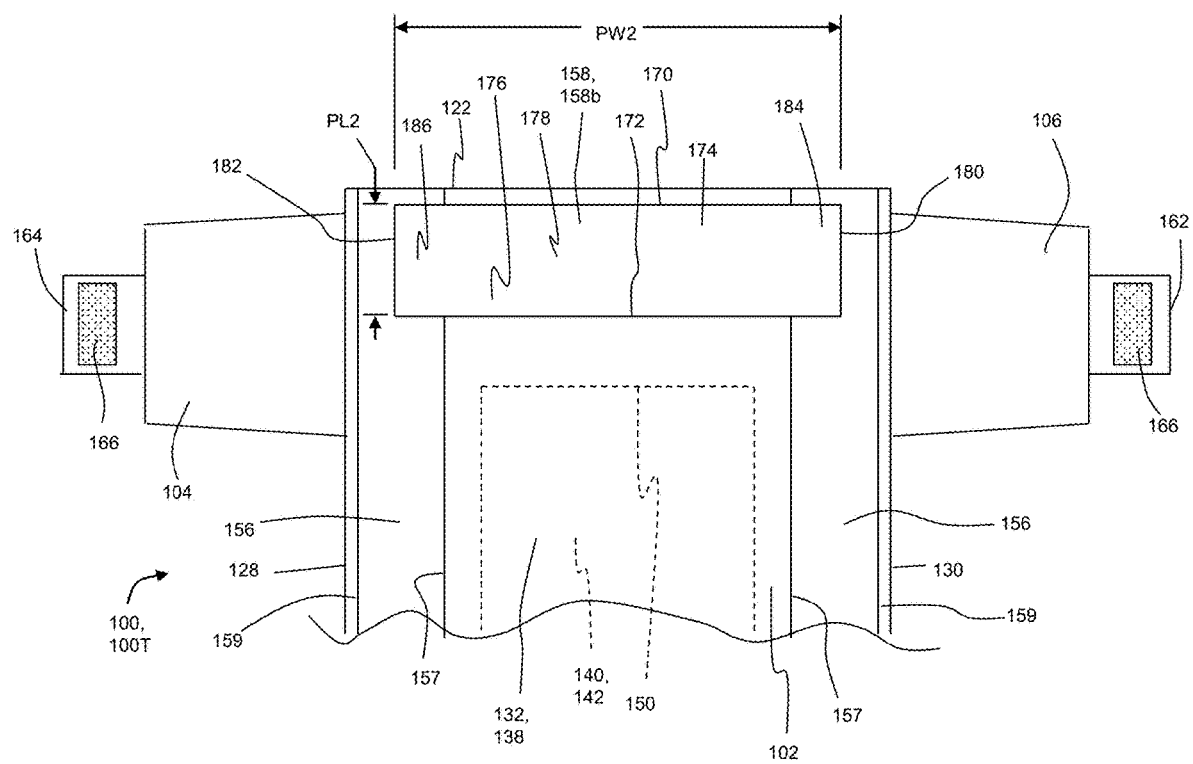
FIG. 6 is a detailed view of a second waist panel with the portion of the diaper that faces toward a wearer oriented towards the viewer.

As shown in FIGS. 5 and 6, the first and second waist panels 158a, 158b herein may each comprise a first lateral edge 170 and a second lateral edge 172, wherein the second lateral edge 172 is positioned longitudinally inward relative the first lateral edge 170. In addition, the first and second waist panels 158a, 158b may comprise a first longitudinal end region 174 adjacent the first lateral edge 170 and a second longitudinal end region 176 adjacent the second lateral edge 172, wherein the first and second longitudinal end regions 174, 176 are separated by a central region 178. The first and second lateral edges 170, 172 may be connected with and separated by a first longitudinal edge 180 and a second longitudinal edge 182. As such, the first and second waist panels 158a, 158b may also include a first lateral end region 184 adjacent the first longitudinal edge 180 and a second lateral end region 186 adjacent the second longitudinal edge 182, wherein the first and second lateral end regions 184, 186 are separated by the central region 178. In some configurations, the first lateral edge 170, second lateral edge 172, first longitudinal edge 180, and/or second longitudinal edge 182 may be defined by a fold line, wherein one or more layers of waist panel 158 may have been folded onto itself or another layer during assembly. In some configurations, the first lateral edge 170, second lateral edge 172, first longitudinal edge 180, and/or second longitudinal edge 182 may be defined by unfolded edge or a cut line, wherein one or more layers of waist panel 158 may have been cut or trimmed during assembly.

The waist panels 158 herein may be configured with various shapes and/or sizes. In embodiments where the absorbent article comprises multiple waist panels, the panels may have the same or different dimensions. For example, as shown in FIGS. 5 and 6, the first waist panel 158a may comprise a first width PW1 extending between first and second longitudinal edges 180, 182, and the second waist panel 158b may comprise a second width PW2 extending between first and second longitudinal edges 180, 182. The first width PW1 and the second width PW2 may be equal or different. In some configurations, the first width PW1 and/or the second width PW2 may be from about 80 mm to about 250 mm, specifically reciting all 1 mm increments within said range and all ranges formed therein or thereby. The first waist panel 158a may comprise a first length PL1 extending between first and second lateral edges 170, 172, and the second waist panel 158b may comprise a second length PL2 extending between first and second lateral edges 170, 172.

The first length PL1 and the second length PL2 may be equal or different. In some configurations, the first length PL1 and/or the second length PL2 may be from about 5 mm to about 80 mm, specifically reciting all 1 mm increments within the said range and all ranges formed therein or thereby.

The waist panels 158 may be located in various lateral and longitudinal positions relative to various absorbent article components. The waist panel 158 may be positioned such that the first and/or second longitudinal edges 180, 182 of the waist panel 158 are located laterally inboard of the leg gasketing elements 156, overlapping the leg gasketing elements 156, or suitable combinations. In some configurations, the first waist panel 158a may be positioned longitudinally inboard from the first waist edge 120 of the absorbent article 100 and/or toward or overlapping the first lateral edge 148 of the absorbent core 142; and the second waist panel 158b may be positioned longitudinally inboard from the second waist edge 122 of the absorbent article 100 and/or toward or overlapping the second lateral edge 150 of the absorbent core 142.

The first waist panel 158a and/or the second waist panel 158b may be bonded with the chassis 102 and/or leg gasketing elements 156 in various ways, such as for example, by adhesive bonds 188, ultrasonic bonds, pressure bonds 190, thermal bonds or combinations thereof. In some configurations, the first waist panel 158a and/or the second waist panel 158b may be continuously bonded with the chassis 102 and/or leg gasketing elements 156 with adhesive or bonded discontinuously with a patterned adhesive. In some configurations, the first waist panel 158a and/or the second waist panel 158b may be mechanically (pressure) bonded with the chassis 102 and/or leg gasketing elements 156 with the application of pressure (and optionally heat). In some configurations, the first waist panel 158a and/or the second waist panel 158b may be mechanically (pressure) bonded with the chassis 102 and/or leg gasketing elements 156 with the use of ultrasonic bonding methods.

Figure 5A:
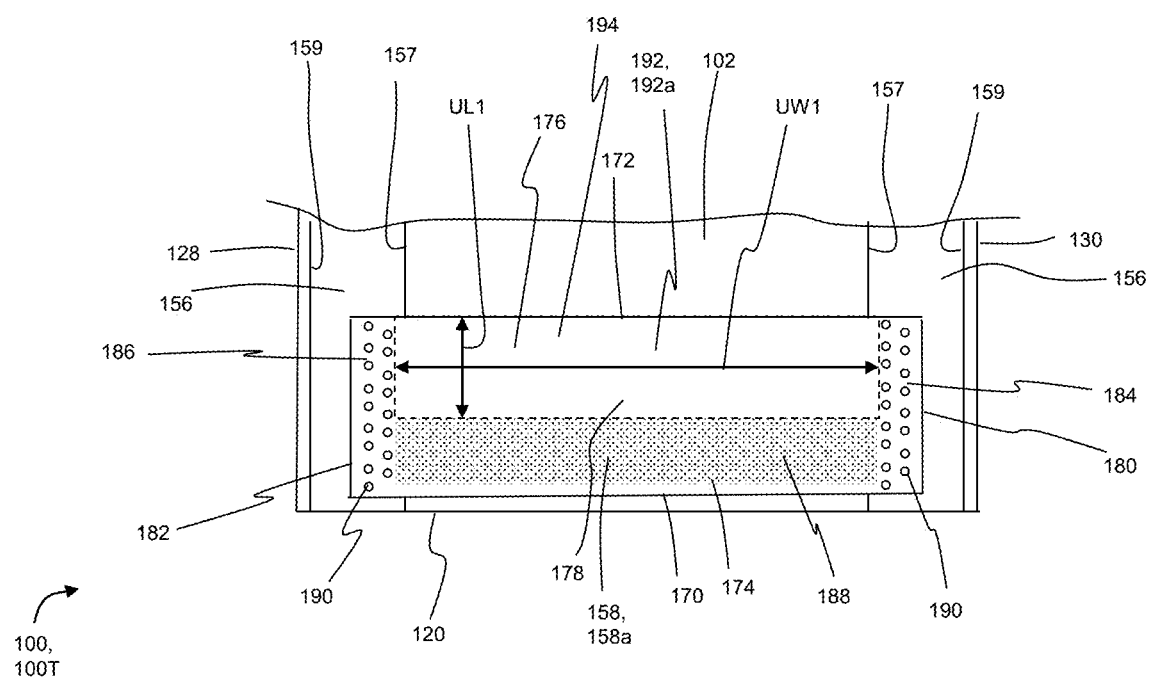
FIG. 5A is a detailed view of the first waist panel from FIG. 5 illustrating bonding configurations.
Figure 6A:
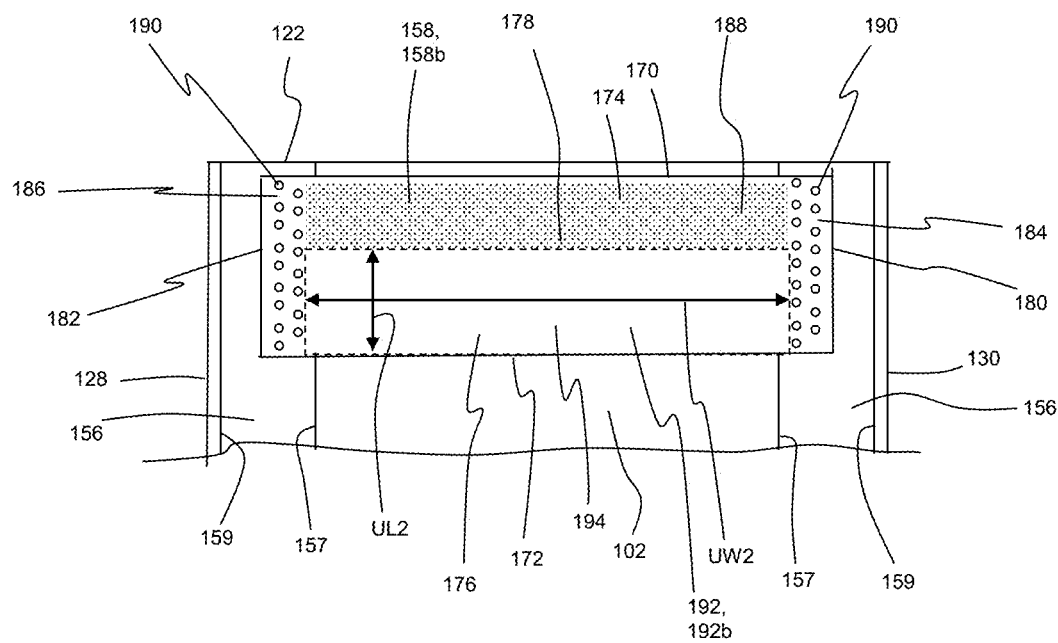
FIG. 6A is a detailed view of a second waist panel from FIG. 6 illustrating bonding configurations.

In some configurations, one or more regions of the waist panel 158 (referred to herein as bond regions) may be bonded with the chassis 102 and/or leg gasketing elements 156, and one or more regions of the waist panel 158 (referred to as unbonded regions 192) may not be bonded (unattached) with the chassis 102 and/or leg gasketing elements 156, thereby forming a pocket 194 between the waist panel 158 and the chassis 102. For example, as shown in FIG. 5A, the first waist panel 158a may comprise bonded regions wherein the first longitudinal end region 174, the first lateral end region 184, and the second lateral end region 186 of the first waist panel 158a are bonded with chassis 102 and/or leg gasketing elements 156; and the first waist panel 158a may comprise at least one unbonded region 192a (generically illustrate by a rectangle with a dashed border) wherein a portion of the second longitudinal end region 176 and at least a portion the second lateral edge 172 may be unattached to the chassis 102 and/or leg gasketing elements 156. A second waist panel 158b may be similarly configured as shown in FIG. 6A with a second unbonded region enumerated as 192b. An unbonded region may comprise various shapes and/or sizes. For example, as shown in FIGS. 5A and 6A, an unbonded region 192 may comprise a laterally extending width UW which may be from about 40 mm to about 200 mm, specifically reciting all 1 mm increments within the above-recited range and all ranges formed therein or thereby. The unbonded region may further comprise a longitudinally extending length UL, which may be from about 10 mm to about 50 mm, specifically reciting all 1 mm increments within the above-recited range and all ranges formed therein or thereby. To the extent the article comprises two waist panels and each comprise an unbonded region 192a, 192b, the unbonded regions may have the same or different dimensions. That is, the first waist panel may have a length UL1 and width UW1 which may be the same or different from the length UL2 and width UW2 of the second waist panel, respectively.

As discussed above, the waist panels 158 herein may be elastic and may comprise at least one direction of stretch. In some configurations, the direction of stretch may be laterally oriented between the first longitudinal edge 180 and the second longitudinal edge 182. In some configurations, the first waist panel 158a and/or the second waist panel 158b may be configured to extend at least about 10 mm with an applied force greater than 0 to about 3N. It is also to be appreciated that the first waist panel 158a may comprise stretch characteristics that are the same or different from stretch characteristics of the second waist panel 158b. Such stretch characteristics may comprise a percent contraction or a percent elongation. In some configurations, the stretch characteristics of the first waist panel 158a may be the same or may vary between the first lateral edge 170 and the second lateral edge 172 and/or the between the first longitudinal edge 180 and the second longitudinal edge 182. And in some configurations, the stretch characteristics of the second waist panel 158b may be the same or may vary between the first lateral edge 170 and the second lateral edge 172 and/or the between the first longitudinal edge 180 and the second longitudinal edge 182.

The desired stretch characteristics of the waist panels 158 herein may be imparted to the waist panels 158 in various ways, such as before, during, or after the waist panel 158 is combined with chassis 102 and/or the leg gasketing elements 156. For example, structural features 196 may be imparted to one or more individual components of the waist panel 158 before, during, and/or after assembly of the waist panel 158 to provide desired stretch characteristics of the waist panel 158. In some configurations, structural features may be imparted to the waist panel 158, the chassis 102, and/or the combined waist panel 158 and chassis 102 to provide desired stretch characteristics of the waist panel 158. In some configurations, the same structural features may be imparted to the first waist panel 158a and/or the second waist panel 158b to help ensure the first and second waist panels 158a, 158b comprise similar stretch characteristics. In some configurations, different structural features may be imparted to the first waist panel 158a and/or the second waist panel 158b to help ensure the first and second waist panels 158a, 158b comprise different stretch characteristics. Additional details regarding structural features are discussed below.

Structural Features

As noted, a side panel and/or a waist panel may comprise one or more structural features 196. The structural features 196 may be formed through modifications of the laminate itself, or may be formed through modifications 195 to individual layers of the laminate. Structural features may provide enhanced breathability, strength, extensibility, stiffness, softness, z-directional resilience, caliper and/or tear resistance in one or more areas of the laminate. In various embodiments, a structural feature is formed from the combination of structural modifications on two or more layers of the laminate and is therefore present on two or more layers of the laminate.

Figure 8:
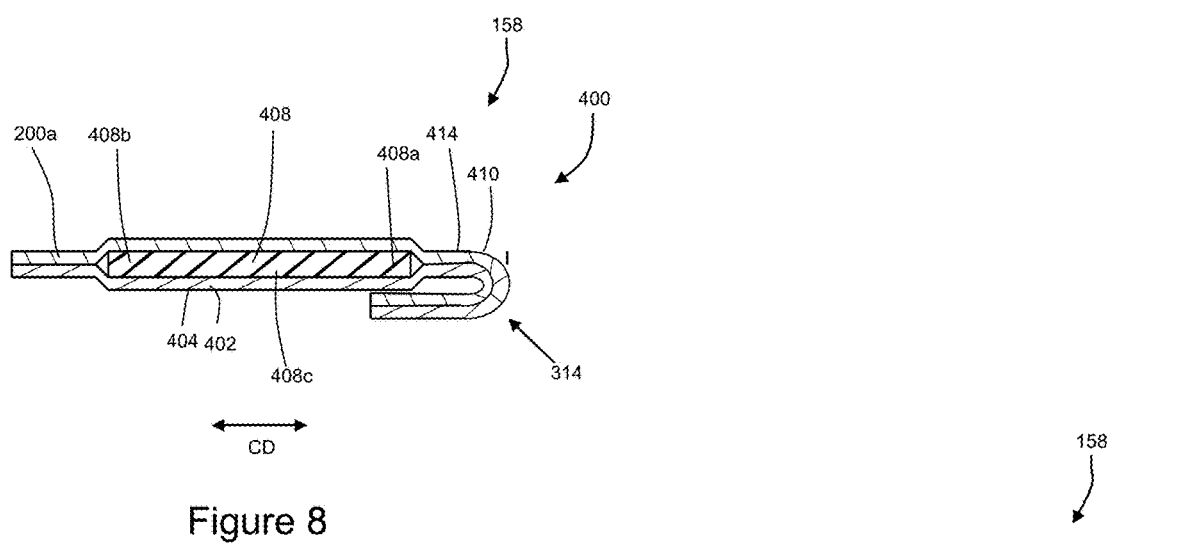
FIG. 8 is a cross sectional view of the elastic substrate from FIG. 7A taken along line 8-8.

FIGS. 2B-2C show examples of structural features disposed on a side panel (i.e., an ear structural feature 196c, 196d). Structural features 196 and/or surface modifications 195 may comprise embossing 302, cuts 304 (e.g., apertures, perforations, slits), melted material or coatings 306, compressed material 308, plastic deformation 310 (e.g., activation stripes 312), folds 314 (see FIGS. 8-9), post-formation bonds 316 (e.g., adhesive bonds, pressure bonds, thermal bonds, and/or ultrasonic bonds applied after the substrate is formed) and combinations thereof. A structural feature or a surface modification may be in the form a design element 320. One or more surface modifications on laminate layers may combine or work together to form a structural feature 196d in the final laminate. For instance, the surface modifications on the layers in FIG. 2B may combine to form a structural feature 196d in FIG. 2C. Further, surface modifications on different laminate layers and/or different forms of surface modifications may combine or work together to enhance breathability, strength, extensibility, stiffness, softness, z-directional resilience, caliper and/or tear resistance.

Additionally, or alternatively, structural features may work in conjunction with laminate bond patterns 24 to form a panel design element 320a. For example, in FIG. 2C, the coating 306 is shown to mute the ultrasonic bond pattern 24 surrounding the structural feature 196c, thereby creating a panel design element 320a that highlights the depicted heart graphic.

A structural feature may be visually perceptible (i.e., able to be detected by a human eye with 20/20 vision in lighting at least equal to the illumination of a standard 100 watt incandescent white light bulb at a distance of 1 meter). Additionally, or alternatively, a structural feature may be tactilely perceptible.

Figure 5B:
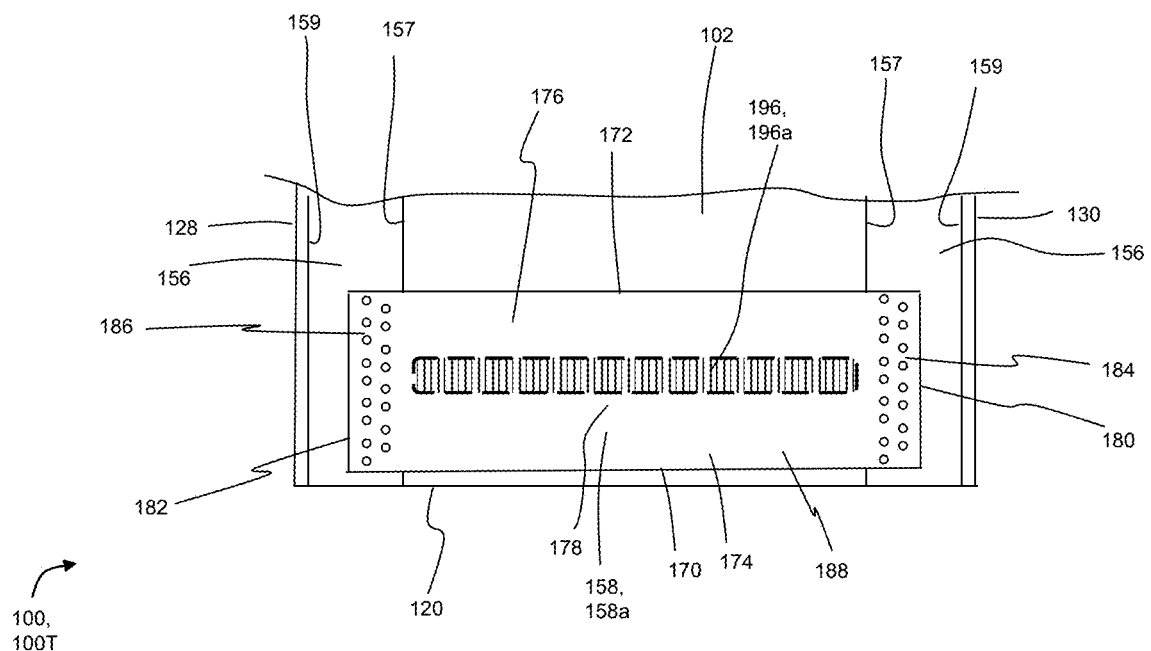
FIG. 5B is a detailed view of the first waist panel from FIG. 5 illustrating structural features.
Figure 5C:
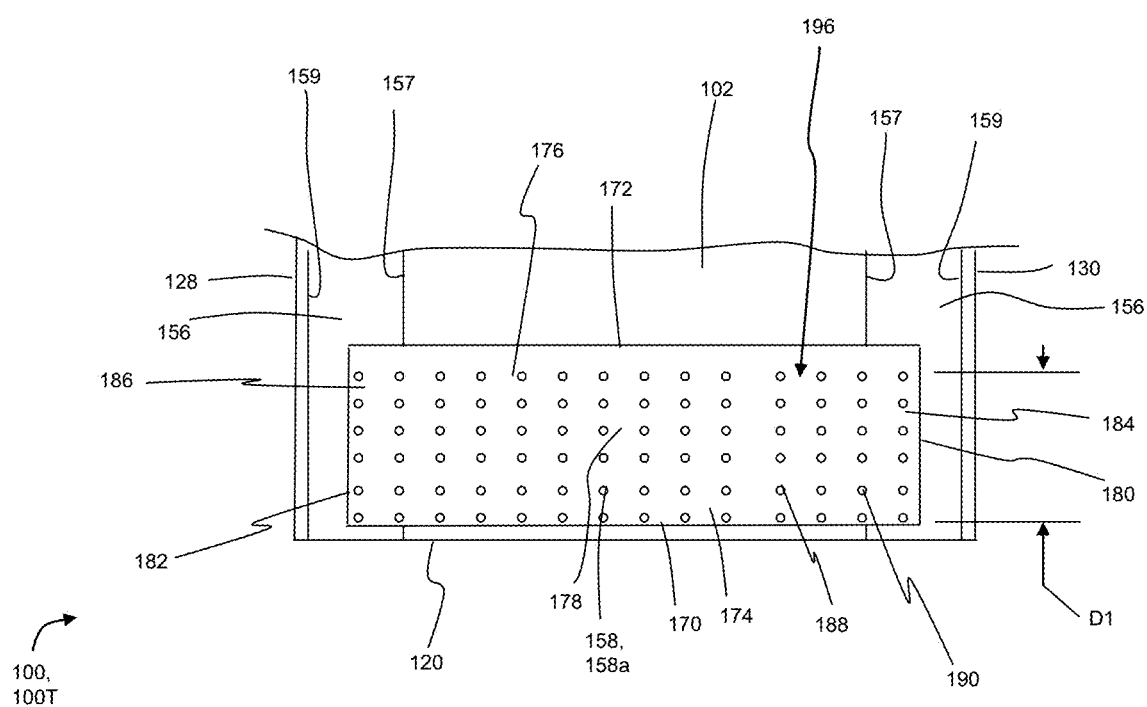
FIG. 5C is a detailed view of the first waist panel from FIG. 5 illustrating a structural feature configuration with pressure bonds.
Figure 6B:
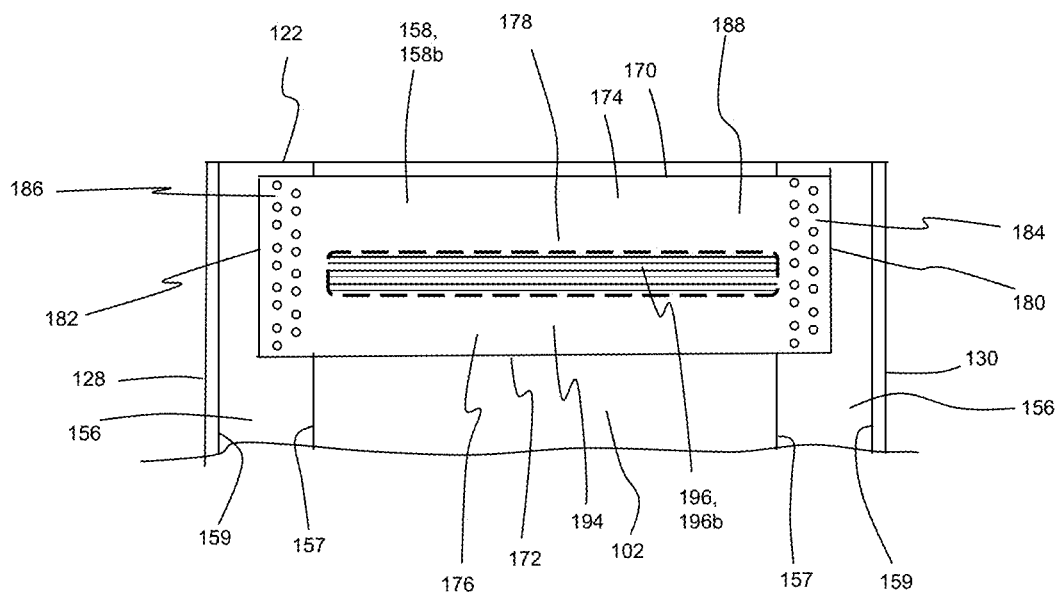
FIG. 6B is a detailed view of a second waist panel from FIG. 6 illustrating structural features.
Figure 6C:
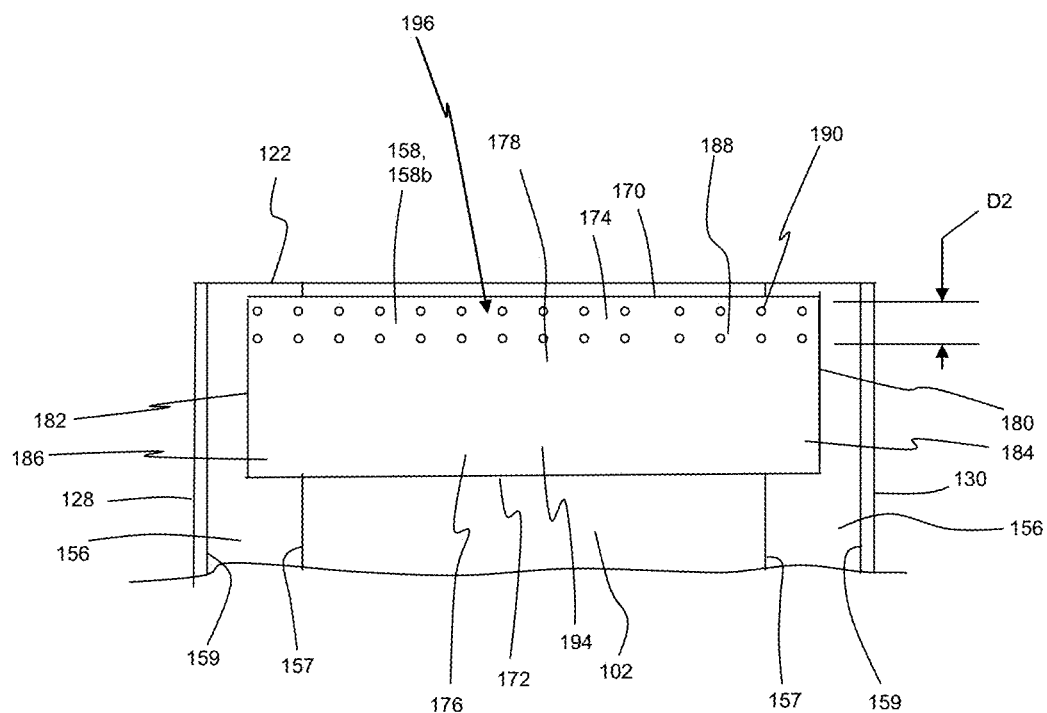
FIG. 6C is a detailed view of a second waist panel from FIG. 6 illustrating a structural configuration with pressure bonds.

FIGS. 5B and 6B show an example absorbent article configuration wherein first waist panel 158a comprises a first structural feature 196a and the second waist panel 158b comprises a second structure feature 196b. The first and second structural features 196a, 196b are generically illustrated as rectangles with patterned fill. Thus, it is to be appreciated that the first structural feature 196a of the first waist panel 158a may be different from the second structural feature 196b of the second waist panel 158b. Likewise, an ear structural feature on a side panel may differ from an ear structural feature on another side panel and/or from a structural feature on a waist panel.

In some configurations, structural features in one elastic panel may correspond to structural features in another panel. For example, a structural feature in a side panel may correspond to a structural feature in a waist panel in appearance and/or feel. The structural features may correspond in pattern, design element, the type of structural feature imparted, the relative surface area of the structural feature to the panel, and combinations thereof.

Returning to FIG. 2C, the laminate 400 (whether in the form of a side panel or waist panel) may comprise a first region 10 and a second region 12. The structural feature may be present in the first region, and the second region may be void of structural features. For the avoidance of doubt, void means that the structural features are absent not merely rearranged (e.g., if the first and second regions merely comprised differing bond patterns, the second region would not be void of the structural feature of bonding). By having one region of the laminate void of the particular structural feature present in another region, the structural feature(s) may be used to impart differences in properties to the regions of the laminate. For example, the first region may differ from the second region in at least one of the following properties: breathability, strength, extensibility, stiffness, softness, z-directional resilience, caliper and tear resistance. In nonlimiting examples, the first region 10 may at least partially, or fully, overlap with the primary region 18. The first region may at least partially, or fully, overlap with the elastic region 32. Additionally, or alternatively, the second region 12 may at least partially, or fully, overlap an inelastic region 20. In some configurations, the second region 12 may at least partially, or fully, overlap an unstretched region 34. Any workable combinations are within the scope of the invention. For instance, the first region 10 may at least partially, or fully, overlap an unstretched zone and the second region may at least partially, or fully, overlap the elastic region.

Additionally, or alternatively, structural features in different article components may differ and thereby impart different properties to the components. For example, in FIGS. 5B and 6B, the first structural feature 196a and the second structural feature 196b may provide different stretch characteristics between the first waist panel 158a and the second waist panel 158b. In another example, the first waist panel 158a may comprise a first structural feature 196a that is not included in the second waist panel 158b, and/or the second waist panel 158b may comprise a second structural feature 196b that is not included in the first waist panel 158a.

It is also to be appreciated that different structural features may be used to impart similar properties to panels (or regions) having different precursor materials or configurations. For instance, unstretched zones 34 may be provided with stretch properties from plastically deforming the substrates in said zone, and thereby provide the unstretched zone with more similar extensibility as an elastic region 32. As another example, one side panel may be formed by ultrasonic bonding resulting in aperturing of the elastomeric layer, while another side panel may be formed with adhesive bonding and void of aperturing in the elastomeric layer. Adding structural features in the form of apertures to the latter side panel after lamination may provide similar breathability to that of the former side panel.

In some configurations, the first structural features 196a and/or the second structural features 196b may be formed by cutting and removing discrete pieces from laminate 400. In some configurations, the first structural feature 196a and/or the second structural feature 196b comprise an amount by which the first waist panel 158a and/or the second waist panel 158b is stretched when bonded with the chassis 102 and/or leg gasketing elements 156. For example, the first waist panel 158a and the second waist panel 158b may be bonded with the chassis 102 in a stretched state, wherein the first waist panel 158a is stretched less than or greater that the second waist panel 158b when bonded with the chassis 102. In some configurations, a stiffening element may be used to provide different stretch characteristics between the first waist panel 158a and the second waist panel 158b. For example, the stiffening element may be disposed on the first waist panel 158a and/or the second waist panel 158b. In some configurations, the stiffening element may comprise a substrate, such as for example, a discrete patch of nonwoven.

In some configurations, the first waist panel 158a and the second waist panel 158b may comprise the same structural features 196 in different areas and/or regions so as to impart different stretch characteristics. For example, the first waist panel 158a may comprise a first structural feature 196a adjacent the first lateral edge 170 and the second waist panel 158b may comprise the same first structural feature 196a adjacent the first lateral edge 170, wherein the first structural feature 196a may extend for different longitudinal lengths and/or lateral widths on the first waist panel 158a and the second waist panel 158b.

FIGS. 2C and 3C shows an example illustration wherein the first waist panel 158a comprises comprising a structural feature 196 in the form of pressure bonds 190, and the second waist panel 158b comprises the same structural feature 196 in the form of pressure bonds 190. A first region of pressure bonds 190 may extend longitudinally inboard from the first lateral edge 170 of the first waist panel 158a by a first distance D1 and a second region of pressure bonds 190 may extend longitudinally inboard from the first lateral edge 170 of the second waist panel 158b by a second distance D2. In some configurations, the first distance D1 may greater than or less than the second distance D2, and as such, the pressure bonds 190 may impart different stretch characteristics to the first and second waist panels 158a, 158b. It is to be appreciated that the first distance D1 and the second distance D2 may extend for various lengths. In some configurations, the first distance D1 and/or the second distance D2 may extend for the entire lengths PL1, PL2 of the first and/or second waist panels 158a, 158b, respectively. In some configurations, the first distance D1 may extend longitudinally inboard of the first lateral edge 170 of the first waist panel 158a for a distance of 10 mm or less, and/or the second distance D2 may extend longitudinally inboard of the first lateral edge 170 of the second waist panel 158b for a distance of 10 mm or less.

The structural features and surface modifications may be formed in various ways, such as for example, by the application ultrasonic energy, laser energy, mechanical activation, pressure, heat, adhesive, folding, coating, and/or cutting. In some nonlimiting examples, structural features may be formed by mechanical activation by passing the respective substrate under tension between the surfaces of a pair of stretching members having intermeshing ridges and valleys, or other features as described in, for example, U.S. Pat. Pub. Nos. 2018/0228668, 2018/0228666A1, 2018/0228669. U.S. Pat. Pub. No. 2013/0082418, U.S. Pat. No. 5,167,897 and/or U.S. Pat. No. 5,993,432. Mechanical activation may be used to create plastic deformations which may be in the form of three-dimensional elements (having a z-directional height greater than the average height of the substrate), activation stripes, compressed regions, and/or apertures for example. Mechanical activation may be used to pre-activate a substrate or elastomeric layer, as disclosed for example in U.S. Patent Pub. Nos. 2017/0296399A1 and U.S. Pat. No. 10,485, 713. A substrate may be overbonded and overbonds may be ruptured through mechanical bonding to create apertures as disclosed in U.S. Pat. Pub. No. 2016/0136014.

In some configurations, the laminate may be mechanically activated to impart stretch, or deform the laminate, in a direction other than the stretch direction. The laminate may, for example, be mechanically activated in a direction perpendicular to the stretch direction. For example, in during lamination, an elastomeric layer may be stretched in the cross direction CD. After lamination, the laminate may be subjected to machine direction MD activation. It is also contemplated that a precursor material (i.e., a substrate 402, 410 or elastomeric material) may be activated before lamination in a direction different than the stretch direction imparted during lamination.

A structural feature may be provided using laser energy using techniques for severing/removing portions of a component, aperturing, and/or marking or any other suitable use. Exemplary laser energy techniques are disclosed in US Pat. Pub. Nos. 2016/0128874, 2016/0354254, 2017/0266056, 2017/0266057 and U.S. Pat. No. 9,561,669 to Yohn.

Coatings and molten materials may be applied to form structural features. Chemical finishes based on oil, silicone, esters, fatty acids, surfactant etc. can be employed. Softeners such as anionic, cationic or nonionic can also be used to improve drape, and touch. Various coating techniques, like roll coating, screen coating, gravure coating, slot coating, spray coating, can be used to apply finish.

A structural feature may be in the form of bonds. The bonds may be formed by mechanical, including pressure, means. Suitable bonds are formed by dynamic bonding through a pressure biased nip between a patterned element and an anvil member as is disclosed in U.S. Pat. Nos. 4,919,738 and 7,056,404 and U.S. Pat. Pub. No. 2015/0173961. In nonlimiting examples, said bonds are formed under pattern element loading pressure of about 20,000 psi to about 200,000 psi at high line speeds. Additionally, or alternatively, bonds may be formed using adhesive which may be applied through spray guns, slot coating or other known processes.

FIGS. 7A-7D show various schematic views of an apparatus 500 operating to assemble a continuous elastic substrate 200a from which discrete laminates of the present invention may be cut. It is to be appreciated that the continuous elastic substrate 200a and the laminates herein may be configured in various ways and may include one or more elastic materials, such as for example, elastic film and/or strands. For example, the continuous elastic substrate 200a may be configured as a single layer of elastic film. In some configurations, the continuous elastic substrate 200a may be configured as a laminate of two more substrates. For example, the continuous elastic substrate 200a may be configured as an elastic film bonded in between two or more nonwoven substrates and/or may be bonded with one or more nonwoven substrates. For example, the continuous elastic substrate 200a may be configured as a bi-laminate with an elastic film bonded with a single nonwoven substrate. In another example, the continuous elastic substrate may be configured as an elastic film bonded between two or more substrates, wherein the substrates may comprise nonwovens. It is also to be appreciated that nonwoven substrates of the elastic substrate may be of the same or different material and/or basis weights.

It is also to be appreciated that the continuous elastic substrate 200a may be assembled in various ways, such as for example, as disclosed in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, which are all incorporated by reference herein. For example, FIGS. 7A-7D show various schematic views of an apparatus 500 operating to assemble a continuous elastic substrate 200a from which the discrete laminates may be cut. In various embodiments, the cross direction CD corresponds to the lateral direction of the laminate in the assembled article.

Figure 7A:
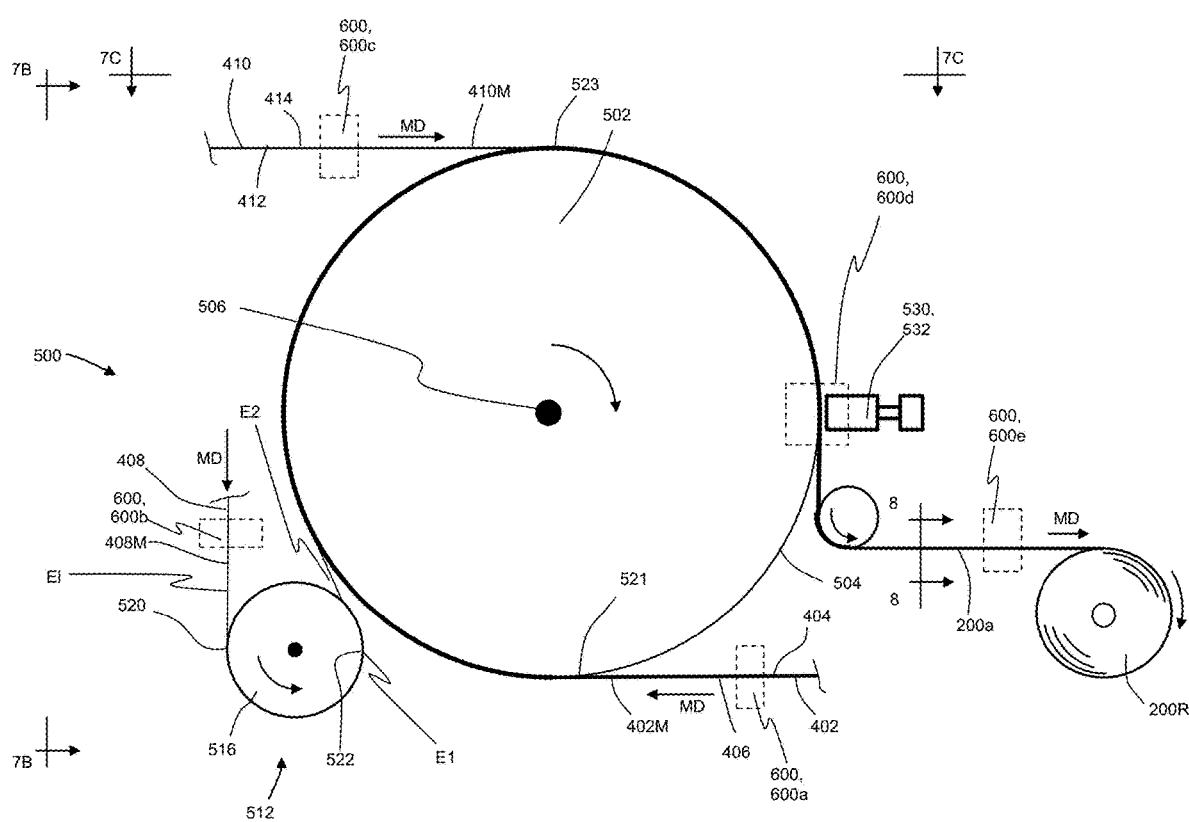
FIG. 7A is a schematic side view of an apparatus operating to assemble an elastic laminate.
Figure 7B:
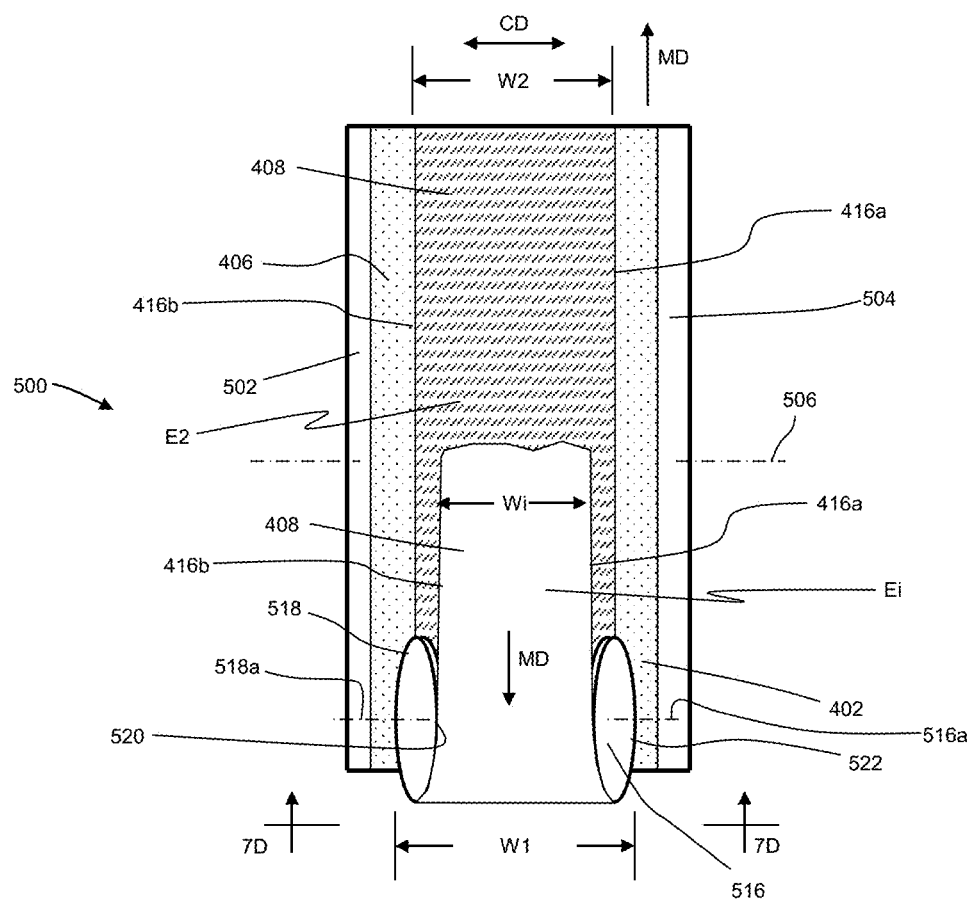
FIG. 7B is a left side view of the apparatus from FIG. 7A taken along line 7B-7B with the transformational apparatus removed.
Figure 7C:
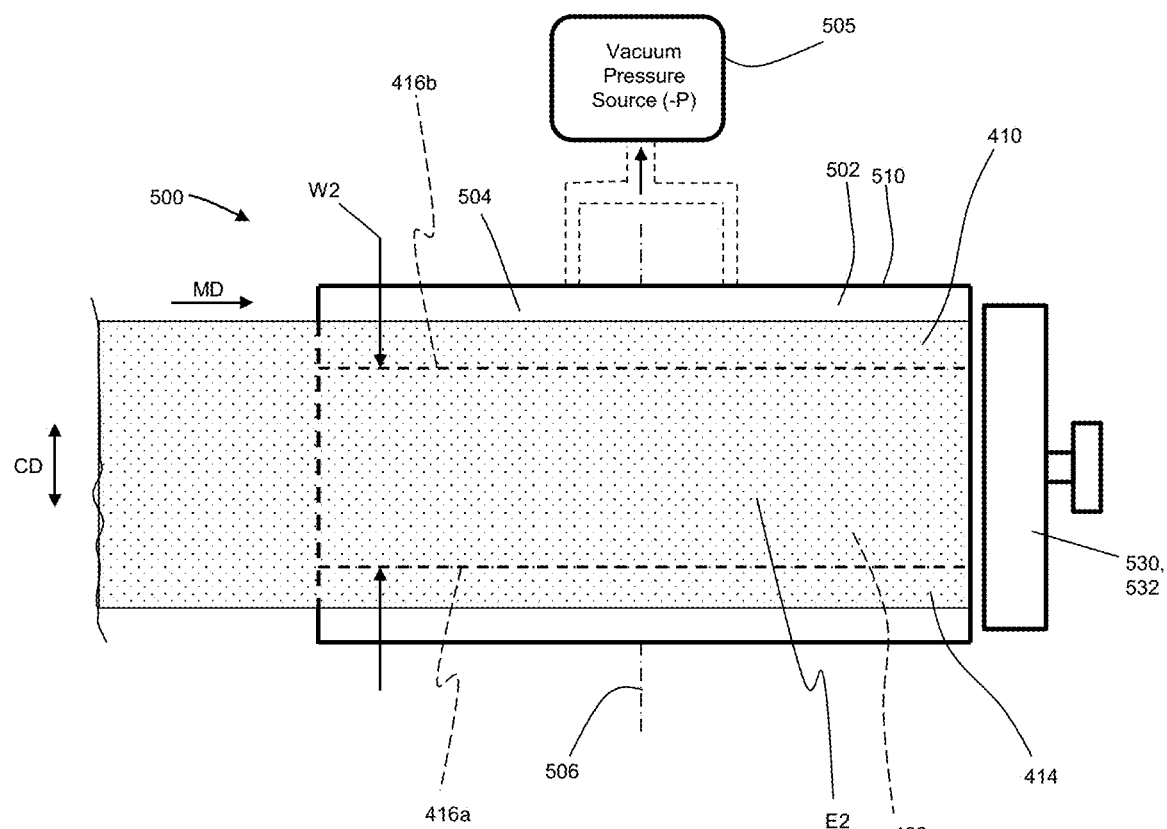
FIG. 7C is a top side view of the apparatus from FIG. 7A taken along line 7C-7C with the transformational apparatus removed.

As shown in FIGS. 7A-7C, a first substrate 402 advances in a machine direction MD onto a rotating anvil 502. More particularly, the first substrate 402 includes a first surface 404 and an opposing second surface 406, and the first substrate 402 advances to wrap the first surface 404 onto an outer circumferential surface 504 of the rotating anvil 502. During the assembly process, a spreader mechanism 512 stretches an elastic film 408 by stretching the elastic film 408 to a first elongation in the cross direction CD. And the stretched elastic film 408 is positioned into contact with the second surface 406 of the first substrate 402. In turn, the elastic substrate 200a may be formed by ultrasonically bonding the first substrate 402 and the elastic film 408 together with a second substrate 410 on the anvil 502. More particularly, the second substrate 410 includes a first surface 412 and an opposing second surface 414, and the second substrate 410 advances to position the first surface 412 in contact with the elastic film 408 and the second surface 406 of the first substrate 402.

With continued reference to FIGS. 7-7C, as the anvil 502 rotates, the first substrate 402, the elastic film 408, and the second substrate 410 are advanced between the outer circumferential surface 504 of the anvil 502 and one or more ultrasonic devices 530 adjacent the anvil 502. It is to be appreciated that the ultrasonic device 530 may include a horn 532 and may be configured to impart ultrasonic energy to the combined substrates and elastic films on the anvil 502. It is to be appreciated that aspects of the ultrasonic bonding device 530 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device 530 may be configured as a linear oscillating type sonotrode, such as for example, available from Herrmann Ultrasonic, Inc. In some configurations, the sonotrode may include a plurality of sonotrodes nested together in the cross direction CD. In turn, the ultrasonic horn 532 bonds the first substrate 404, the elastic film 408, and the second substrate 410 together to form the elastic substrate 200a.

Figure 9:
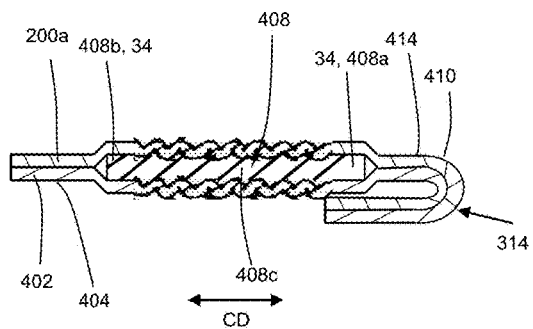
FIG. 9 is a cross-sectional view of the elastic substrate from FIG. 8 in a relaxed, contracted condition.

As shown in FIG. 7A, the elastic substrate 200a may then advance from the anvil 502 and may be accumulated, such as for example, by being wound onto a roll 200R or being festooned in a container. It is to be appreciated that the elastic substrate 200a may be wound onto a roll 200R in a fully stretched, partially stretched, or fully relaxed state. The accumulated elastomeric substrate 200a may be stored and/or moved to a location for incorporation into an absorbent article assembly process wherein the elastomeric substrate 200a may be converted into an absorbent article component, such as discussed above. It is also to be appreciated that the elastic substrate 200a may advance from the anvil 502 and directly to absorbent article assembly processes. FIG. 9 also shows the elastic substrate 200a in a relaxed state wherein the central region 408c of the elastic film 408 is contracted in the cross direction CD. It is to be appreciated that the apparatus 500 may be configured to assemble elastic substrates 200a with a single lane of elastic film 408 and may also be configured to assemble elastic substrates 200a with multiple lanes of elastic film 408 separated from each other in the cross direction. In turn, the elastic substrate 200a may be cut along the machine direction MD between such lanes of elastic films 408 to create multiple individual elastic substrates 200a.

During the ultrasonic bonding process, it is to be appreciated that bonds imparted into the elastic substrate 200a from the ultrasonic horn 532 may correspond with patterns and/or shapes defined by a plurality of pattern elements extending radially outward from the outer circumferential surface 504 of the anvil 502. It is to be appreciated that the elastic substrate 200a may include various portions of components bonded together in various ways and with differing or identical bond patterns. For example, the elastic film 408 may be bonded together with the first and/or second substrates 402, 410, and the first substrate 402 may be bonded directly to the second substrate 410 in areas of the elastic substrate 200a. In some configurations, the first and second substrates 402, 410 may be bonded directly to each other through apertures in the elastic film, wherein such apertures may be formed during the bonding process. In some configurations, the elastic film 408 can be involved, or participate, in the bonding between the first and second substrates 402, 410, wherein "involved" can mean that the elastic film can, to some extent, be in intimate contact with, and possibly partially merged with, one or both the first and second substrates 402, 410. The involvement may be due to actual melt bonding about the perimeter of a bond site or may be due to mechanical interaction, such as by entanglement of a fibrous elastic layer between fibrous nonwoven layers also about the perimeter of bond site. It is to be appreciated that the apparatus 500 may be adapted to create various types of bond configurations, such as disclosed, for example, in U.S. Pat. Nos. 6,572,595; 6,830,800; 7,087,287; and 7,803,244; and U.S. Patent Publication Nos. 2018/0042778 A1; 2018/0042787 A1; 2018/0042779 A1; and 2018/0042780 A1, which are all incorporated by reference herein.

Figure 7D:
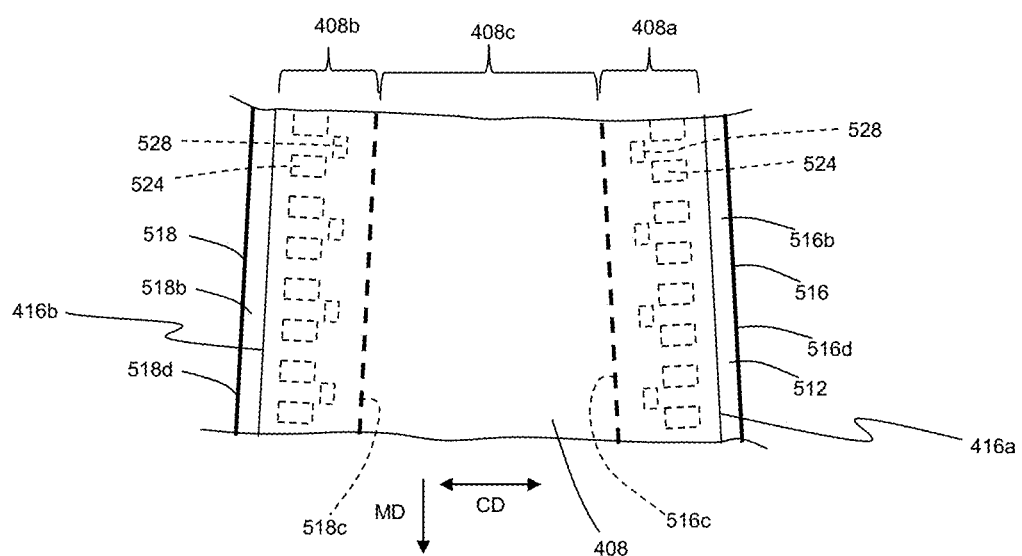
FIG. 7D is a detailed view of an elastic material advancing on a spreader mechanism from FIG. 7B taken along line 7D-7D.

As previously mentioned, the spreader mechanism 512 stretches the elastic film 408 to a first elongation E1 in the cross direction CD. With particular reference to FIGS. 7A and 7D, the elastic film 408 includes a first edge 416a and a second edge 416b separated from the first edge 416a in the cross direction CD. In addition, the elastic film 408 includes a first edge region 408a adjacent the first edge 416a and a second edge region 408b adjacent the second edge 416b. The first edge region 408a is separated from the second edge region 408b in the cross direction CD by a central region 408c. As shown in FIGS. 7A and 7B, the elastic film 408 may define an initial width Wi in the cross direction CD between the first edge 416a and the second edge 416b upstream of the spreader mechanism 512. The elastic film 408 advances in a machine direction MD onto the spreader mechanism 512 at a first location 520. The elastic film 408 may be at the initial width Wi in the cross direction CD while advancing onto the spreader mechanism 512. The elastic film 408 may be in a relaxed state upstream of the spreader mechanism 512.

As shown in FIGS. 7B and 7D, the first edge region 408a of the elastic film 408 advances onto an outer rim 516b of a first disk 516 of the spreader mechanism 512, and the second edge region 408b advances onto an outer rim 518b of a second disk 518. In addition, the outer rim 516b of the first disk 516 may extend axially between an inner edge 516c and an outer edge 516d, and the outer rim 518b of the second disk 518 may extend axially between an inner edge 518c and an outer edge 518d. The outer rims 516b, 518b of the first and second disks 516, 518 of the spreader mechanism 512 may include channels 524 fluidly connected to a vacuum pressure source and may include radially protruding nubs 528. Thus, as shown in FIG. 7D, the first edge region 408a of the elastic film 408 may be held in position on the outer rim 516b with vacuum air pressure in the channels 524 and with the radially protruding nubs 528. Similarly, the second edge region 408b of the elastic film 408 may be held in position on the outer rim 518b with vacuum air pressure in the channels 524 and with the radially protruding nubs 528. Thus, the first and second edge regions may generally correspond with unstretched regions 34 in the laminate 400.

With continued reference to FIGS. 7B and 7D, the first disk 516 and the second disk 518 are canted. Thus, as the first disk 516 and the second disk 518 of the spreader mechanism 512 rotate, the elastic film 408 is stretched in the cross direction CD while advancing from the first location 520 or downstream of the first location 520 toward a second location 522. Thus, as shown in the FIGS. 7A, 7B, and 7D, the spreader mechanism 512 may stretch the elastic film 408 in the cross direction CD from the initial width Wi (and an initial elongation Ei) to a first width W1 (and a first elongation E1) in the cross direction CD, wherein W1 is greater than Wi and wherein E1 is greater than Ei. In some configurations, the elastic film 408 may be consolidated to a second width W2 (and second elongation E2), wherein W2 is less than W1 and wherein E2 is less than E1. It is to be appreciated that the elastic film 408 remains stretched at the second width W2 (and second elongation E2). It is also to be appreciated that the elastic film 408 may be in a relaxed state at the initial width Wi (and initial elongation Ei), and as such, the second width W2 may be greater than the initial width Wi and the second elongation E2 may be greater than the initial elongation Ei. In configurations where the elastic film is not consolidated, W2 may be equal to W1 and E2 may be equal to E1.

In some configurations, when the spreader mechanism includes canted disks, the first and second edge regions 408a, 408b of the elastic film 408 may be held in position on the outer rims 516b, 518b of the disks 516, 518. And as such, some portions of the first and second edge regions 408a, 408b may remain unstretched in the cross direction CD as the first and second disks 516, 518 rotate. Thus, as the first disk 516 and the second disk 518 of the first spreader mechanism 512 rotate, the central region 408c of the elastic film 408 is stretched in the cross direction CD.

As shown in FIG. 7A-7D, the elastic film 408 advances from the spreader mechanism 512 downstream of the second location 522 to the anvil 502, and onto the second surface 406 of the first substrate 402 on the anvil 502. And as the anvil 502 rotates, the second substrate 410 advances onto anvil 502 to position the first surface 412 in contact with elastic film 408 and the second surface 406 of the first substrate 402 to form an elastic substrate 200a and the first substrate 402, elastic film 408, and second substrate 410 are bonded together.

With continued reference to FIGS. 7A and 7B, the outer circumferential surface 504 of the anvil 502 may be fluidly connected with a vacuum source 505, and as such, vacuum air pressure may be applied to the first substrate 402 on the anvil 502. For example, the outer circumferential surface 504 of the anvil roll 502 may include a plurality of apertures fluidly connected with the vacuum pressure source. When the first substrate 402 is configured as a porous substrate, such as a nonwoven, vacuum air pressure may also be applied to the elastic film 408 on the anvil 502, and as such, may help maintain the stretched condition of the the elastic film 408 while on the anvil 502. In some configurations, adhesive on a nonwoven may also help decrease the porosity of the nonwoven, which in turn, may enhance the ability of the vacuum air pressure to help maintain components in a stretched state.

As mentioned above, the elastic substrate 200a (and laminates) may include nonwoven substrates that may be of the same or different material and/or basis weights. For example, the first substrate 402 and the second substrate 410 referred to above with reference to FIGS. 7A-9 may be configured as nonwoven substrates. As such, the first substrate 402 and the second substrate 410 of the elastic substrate 200a and discrete laminates 400 may be the same or different types of nonwovens and/or may have the same or different basis weights. In addition, the carrier substrate 202 may include one or more nonwoven substrates. As such, the first substrate 402 and/or the second substrate 410 of the elastic substrate 200a and elastic laminates 400 may be the same or different types of nonwovens and/or may have the same or different basis weights as a nonwoven substrate of the carrier substrate 202. In addition, the nonwoven substrates of elastic substrate 200a and laminates 400, such as the first substrate 402 and/or the second substrate 410 for example, may include nonwoven substrates having the same or different fiber orientations as a nonwoven substrates in other article components (e.g., topsheet, backsheet).

As previously mentioned, apparatuses and methods to assemble the elastic laminates and/or bond the laminates with other absorbent article components may be adapted to assemble absorbent articles 100 with side panel(s) and/or waist panel(s) that include structural features or morphological features that impart enhanced properties or differences in properties in the location of the panel, such properties including for example breathability, softness, strength, extensibility, softness and tear resistance.

In another example, with reference to FIG. 7A, the apparatus 500 may include one or more transformational apparatuses 600 that may be adapted to modify the first substrate 402, the second substrate 410, the elastic layer (e.g., film 408), and/or the assembled elastic substrate 200a. The transformational apparatuses 600 are generically represented in FIG. 7A as dashed line rectangles. As discussed above, the transformational apparatuses 600 may be adapted to form various types of morphological features, such as embossing, apertures, slits, melted material, compressed material, plastic deformations, folds, adhesive bonds, and/or pressure bonds and in various ways, such as for example, by the application ultrasonic energy, mechanical activation, laser energy, pressure, heat, adhesive, folds, and or cuts. As shown in FIG. 7A, the apparatus 500 may include a transformational apparatus 600a upstream of the meeting location 521 at which the first substrate 402 advances onto the anvil roll 502 that may be adapted to impart morphological features to the first substrate, thereby forming a modified substrate 402M (such as a preactivated substrate, apertured substrate, embossed substrate, etc.). Additionally, or alternatively, the apparatus 500 may include a transformational apparatus 600b upstream of the spreader mechanism 512 that may be adapted to impart morphological features to the elastic film 408 thereby forming a modified film 408M (such as an apertured film, preactivated film, embossed film, etc.). In some configurations, a transformational apparatus may be downstream of spreader mechanism 512 that may be adapted to impart morphological features to the stretched elastic film 408. With continued reference to FIG. 7A, the apparatus 500 may include a transformational apparatus 600c upstream of the meeting location 523 of the second substrate and anvil that may be adapted to impart morphological features to the second substrate 410, thereby forming a modified second substrate 410M. The anvil 502 and/or the horn 530 may also be configured as a transformational apparatus 600d that may be adapted to impart morphological features to the elastic film 408, the first substrate 406, and/or the second substrate 410 during bonding operations (other than the actual bonding of the substrates). A transformational apparatus 600e may be positioned downstream of the horn 530 that may be adapted to impart morphological features to the elastic laminate 200a. In nonlimiting examples, the transformational apparatus 600e imparts morphological features extending through the thickness of the final laminate, thereby be present in each laminate layer. It is also contemplated, however, that one or more morphological features imparted to the laminate by transformational apparatus 600e extend through fewer than all laminate layers and/or extend for a z-directional dimension that is less than the maximum thickness of the laminate where said features are present.

A transformational apparatus 600 may impart morphological features to one region of the respective substrate, elastomeric layer, or laminate and not to another region. Suitable registration and/or programming techniques may be used to impart the morphological features in desired locations. Further, while FIG. 7A illustrates transformational apparatuses affecting each laminate layer, it is also contemplated that a surface modification be applied to one layer and another layer be void of a surface modification. Additionally, or alternatively, a surface modification on one layer may not reach or affect another layer. By way of nonlimiting example, a material coated on a first surface of the first substrate may not be in contact with the elastomeric layer or the second substrate.

Likewise, a transformation apparatus 600 may be included as part of an absorbent article assembly apparatuses and may be adapted to modify the elastic substrate 200a, the laminate 400, a portion of the chassis (or precursor chassis material), and/or a composite of the laminate 400 with the chassis/chassis precursor material to create morphological differences that result in morphological differences between the first and second side panels 104, 106 and/or between the first waist panel 158a and the second waist panel 158b.

Transformational apparatuses 600 may be adapted to form various types of morphological and/or surface features, such as embossing, apertures, slits, melted material, compressed material, plastic deformations, folds, adhesive bonds, and/or pressure bonds and in various ways, such as for example, by the application ultrasonic energy, laser energy, pressure, heat, adhesive, folds, and or cuts. It is to be appreciated that morphological features may also include size differences between discrete laminates 400, such as for example, different machine direction (MD) lengths. Suitable configurations for assembly apparatuses having transformation apparatuses are disclosed in commonly assigned U.S. Patent App. No. 63/020,043.

It is to be appreciated that absorbent articles 100 may be assembled with various components, including waist panels 158, described herein in various ways. Suitable methods for assembling absorbent articles with waist panels are disclosed in commonly assigned U.S. Pat. Appl. No. 63/020,043.

Combinations

A. An absorbent article comprising:
a first waist region, a second waist region, and a crotch region disposed between the first and second waist regions;
a chassis comprising a topsheet, a backsheet, and an absorbent core positioned between the topsheet and the backsheet; and
an elastic panel having an elastomeric layer and a substrate and being joined to the chassis in one of the first waist or the second waist regions;
wherein the elastic panel comprises a structural feature comprising at least one of the following: embossing, apertures, perforations, slits, melted material or coatings, compressed material, secondary bonds, plastic deformation, and folds.

B. The absorbent article of paragraph A, wherein the elastic panel comprises a side panel.

C. The absorbent article of any of the preceding claims, wherein the structural feature comprises secondary bonds that are disposed apart from a chassis attachment bond.

D. The absorbent article of any of the preceding paragraphs wherein the elastic panel comprises an ultrasonically bonded, gathered laminate.

E. The absorbent article of any of the preceding claims, wherein the elastic panel comprises a first region and a second region, wherein the structural feature is disposed in the first region but not in the second region, and wherein the first region differs from the second region in at least one of the following properties: breathability, stiffness, strength, extensibility, caliper, z-directional resiliency, softness and tear resistance.

F. The absorbent article of any of the preceding paragraphs comprising a side panel, wherein at least a portion of the side panel comprises printing.

G. The absorbent article of any of the preceding paragraphs, wherein the structural feature is formed by the application of at least one of the following to the elastic panel: ultrasonic energy, laser energy, mechanical activation, pressure, liquid coating, folding, cutting, adhesive and heat.

H. The absorbent article of any of the preceding paragraphs, wherein the structural feature comprises one or more surface modifications imparted to the substrate and/or one or more surface modifications imparted to the elastomeric layer.

I. The absorbent article of paragraph H, wherein the one or more surface modifications are imparted to the substrate and wherein there is no surface modification present in the elastomeric layer.

J. The absorbent article of paragraph I, wherein at least one of the one or more surface modifications comprises apertures, slits or perforations.

K. The absorbent article of paragraphs I or J, wherein at least some of the one or more surface modifications comprise activation stripes.

L. The absorbent article of any of paragraphs A-H, wherein the structural feature extends through the thickness of the laminate and/or through all layers of the laminate.

M. The absorbent article of any of the preceding paragraphs, wherein the elastomeric layer comprise a film.

N. The absorbent article of any of the preceding paragraphs, wherein the substrate comprises a nonwoven.

O. The absorbent article of paragraph N wherein the nonwoven comprises a pre-activated nonwoven.

P. The absorbent article of any of the preceding paragraphs further comprising a second elastic panel, the second elastic panel having an elastic film joined to a nonwoven and a second structural feature, wherein the second structural feature corresponds to the structural feature in one of the group consisting of: pattern, feature type, relative surface area of the respective panel and combinations thereof.

Q. The absorbent article of paragraph P, wherein the second elastic panel is disposed in the one of the first or second waist regions.

R. The absorbent article of paragraphs P or Q, wherein the second elastic panel comprises ultrasonic bonds.

S. The absorbent article of any of the preceding paragraphs, wherein the elastic panel and/or the second elastic panel comprises a waist panel.

T. The absorbent article of paragraph S, wherein the waist panel comprises:
an inboard lateral edge, an outboard lateral edge, and two longitudinal edges; and
wherein regions of the waist panel adjacent the outboard lateral edge and the longitudinal edges are bonded to the chassis and at least a portion of an inboard lateral edge of the first waist panel is unattached to the chassis.

U. The absorbent article of any of the preceding paragraphs, wherein the structural feature comprises a design element.

V. The absorbent article of any of the preceding paragraphs, wherein the substrate and elastomeric layer are joined with bond(s) disposed in a bonding pattern, and the bonding pattern and the structural feature collectively comprise a panel design element.

W. The absorbent article of any of the preceding paragraphs, wherein the elastic panel is extensible in a stretch direction and the structural feature is formed by mechanically activating the elastic panel to create extension in a direction perpendicular to the stretch direction.

X. A method of forming a side panel for an absorbent article; the method comprising steps of:
providing a first substrate and a second substrate, each defining a width in a cross direction;
creating a morphological difference in the first substrate to form a modified substrate;
providing an elastomeric material comprising a first edge region and a second edge region separated from the first edge region in the cross direction by a central region;
stretching the central region of the elastomeric material in the cross direction;
positioning the stretched central region of elastomeric material between the modified substrate and second substrate; and
forming an elastic laminate by ultrasonically bonding the modified substrate together with the stretched central region and the second substrate.

Y. The method of paragraph X, wherein the step of creating the morphological difference is selected from the group of: adhesive bonding, pressure bonding, thermal bonding, ultrasonic bonding, embossing, slitting, aperturing, coating, plastic deforming, folding, and perforating.

Z. The method of paragraphs X or Y, wherein the step of creating the morphological difference further comprises mechanically activating the first substrate.

AA. The method of any of paragraphs X-Z, wherein the step of creating the morphological difference further comprises using ultrasonic energy, pressure, adhesive and/or heat to form bonds and/or compressed material in the first substrate.

BB. The method of any of paragraphs X-AA, wherein the step of creating the morphological difference further comprises cutting the first substrate using laser energy.

CC. A method of forming a side panel for an absorbent article; the method comprising steps of:
providing a first substrate and a second substrate, each defining a width in a cross direction;
providing an elastomeric material comprising a first edge region and a second edge region separated from the first edge region in the cross direction by a central region;
stretching the central region of the elastomeric material in the cross direction;
positioning the stretched central region of elastomeric material between the first and second substrates;
forming an elastic laminate by ultrasonically bonding the first substrate together with the stretched central region and the second substrate; and
creating a morphological difference in a first region of the laminate but not in a second region of the laminate.

DD. The method of paragraph CC further comprising the step of joining the side panel to the absorbent article, wherein the step of creating a morphological difference is performed after the step of joining the side panel to the absorbent article.

EE. The method of paragraphs CC or DD, wherein the step of creating a morphological difference further comprises creating the morphological difference in the film prior to bonding the laminate layers, wherein the morphological difference is selected from the group consisting of: adhesive bonding, pressure bonding, thermal bonding, ultrasonic bonding, embossing, coating, folding, and combinations thereof.

FF. The method of any of paragraphs CC-EE, wherein the step of creating a morphological difference further comprises creating the morphological difference in the first substrate prior to bonding the laminate.

GG. The method of any of paragraphs CC-FF, wherein the step of creating the morphological difference is selected from the group of: adhesive bonding, pressure bonding, thermal bonding, ultrasonic bonding, embossing, slitting, aperturing, coating, plastic deformation, folding, and perforating.

HH. The method of any of paragraphs CC-GG wherein the step of creating the morphological difference further comprises mechanically activating the elastic laminate.

II. The method of paragraph HH, wherein the step of creating the morphological difference further comprises mechanically activating the elastic laminate in the machine direction.

JJ. The method of any of paragraphs CC-HH, wherein the first region is in at least partial overlapping relationship with an unstretched region of the elastic laminate and the second region is in at least partial overlapping relationship with the stretched central region.

Hysteresis Test Method

The Hysteresis Test can be used to various specified strain values. The Hysteresis Test utilizes a commercial tensile tester (e.g., from Instron Engineering Corp. (Canton, MA), SINTECH-MTS Systems Corporation (Eden Prairie, MN) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The specimens are conditioned for 24 hours prior to testing.

The specimen is cut in dimension of 10 mm in the intended stretch direction of the laminate by 25.4 mm in the direction perpendicular to the intended stretch direction of the laminate. The portion of the specimen held between grips should comprise relatively uniform stretch characteristics (i.e., the gripped portion should not include both inelastic and elastic regions).

Test Protocol

1. Select the appropriate grips and load cell. The grips must have flat surfaces and must be wide enough to grasp the specimen along its full width. Also, the grips should provide adequate force and suitable surface to ensure that the specimen does not slip during testing. The load cell is selected so that the tensile response from the specimen tested is between 25% and 75% of the capacity of the load cell used.

2. Calibrate the tester according to the manufacturer's instructions.

3. Set the distance between the grips (gauge length) at 7 mm.

4. Place the specimen in the flat surfaces of the grips such that the uniform width lies along a direction perpendicular to the gauge length direction. Secure the specimen in the upper grip, let the specimen hang slack, then close the lower grip. Set the slack preload at 5 gram/force. This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5(a) First cycle loading: Pull the specimen to the 50% strain at a constant cross head speed of 70 mm/min. Report the stretched specimen length between the grips as $l_{max}$.

5(b) First cycle unloading: Hold the specimen at the 50% strain for 30 seconds and then return the crosshead to its starting position (0% strain or initial sample length, $l_{ini}$) at a constant cross head speed of 70 mm/min. Hold the specimen in the unstrained state for 1 minute.

5(c) Second cycle loading: Pull the specimen to the 50% strain at a constant cross head speed of 70 mm/min.

5(d) Second cycle unload: Next, Hold the specimen at the 50% strain for 30 seconds and then return the crosshead to its starting position (i.e. 0% strain) at a constant cross head speed of 70 mm/min.

A computer data system records the force exerted on the sample during the test as a function of applied strain. From the resulting data generated, the following quantities are reported.

i. Length of specimen between the grips at a slack preload of 5 gram-force ($l_{ini}$) to the nearest 0.001 mm.

ii. Length of specimen between the grips on first cycle at the 50% strain ($l_{max}$) to the nearest 0.001 mm.

iii. Length of specimen between the grips at a second cycle load force of 7 gram-force ($l_{ext}$) to the nearest 0.001 mm.

iv. % Set, which is defined as $(l_{ext}-l_{ini})/(l_{max}-l_{ini})*100\%$ to the nearest 0.01%. The testing is repeated for six separate samples and the average and standard deviation reported.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of forming a side panel for an absorbent article; the method comprising steps of:
providing a first substrate and a second substrate, each defining a width in a cross direction;
creating a morphological difference in a first region of the first substrate but not in a second region of the first substrate to form a modified substrate;
providing an elastomeric material comprising a first edge region and a second edge region separated from the first edge region in the cross direction by a central region;
stretching the central region of the elastomeric material in the cross direction;
positioning the stretched central region of elastomeric material between the modified substrate and second substrate; and
forming an elastic laminate by ultrasonically bonding the modified substrate together with the stretched central region and the second substrate; wherein the first region of the modified substrate is in at least partial overlapping relationship with an unstretched region of the elastic laminate and wherein the second region of the modified substrate is in at least partial overlapping relationship with the stretched central region of the elastomeric material.

2. The method of claim 1, wherein the step of creating the morphological difference is selected from the group consisting of: adhesive bonding, pressure bonding, thermal bonding, ultrasonic bonding, embossing, cutting, coating, plastic deforming, folding, and perforating.

3. The method of claim 2, wherein the step of creating the morphological difference further comprises using ultrasonic energy, pressure, adhesive and/or heat to form bonds and/or compressed material in the first substrate.

4. The method of claim 2, wherein the step of creating the morphological difference further comprises cutting the first substrate using laser energy.

5. The method of claim 1, wherein the first region of the modified substrate differs from the second region of the modified substrate in at least one of the following properties: breathability, stiffness, strength, extensibility, caliper, z-directional resiliency, softness, and tear resistance.

6. A method of forming a side panel for an absorbent article; the method comprising steps of:
providing a first substrate and a second substrate, each defining a width in a cross direction;
providing an elastomeric material comprising a first edge region and a second edge region separated from the first edge region in the cross direction by a central region;
stretching the central region of the elastomeric material in the cross direction;
positioning the stretched central region of elastomeric material between the first and second substrates;
forming an elastic laminate by ultrasonically bonding the first substrate together with the stretched central region and the second substrate; and
creating a morphological difference in a first region of the laminate but not in a second region of the laminate;
wherein the first region is in at least partial overlapping relationship with an unstretched region of the elastic laminate and the second region is in at least partial overlapping relationship with the stretched central region.

7. The method of claim 6 further comprising a step of joining the side panel to the absorbent article, wherein the step of creating a morphological difference is performed after the step of joining the side panel to the absorbent article.

8. The method of claim 6, wherein the step of creating a morphological difference further comprises creating the morphological difference in the elastomeric material prior to bonding the laminate layers, wherein the morphological difference is selected from the group consisting of: adhesive bonding, pressure bonding, thermal bonding, ultrasonic bonding, embossing, coating, folding, and combinations thereof.

9. The method of claim 6, comprises further comprising a step of creating a first substrate morphological difference in the first substrate prior to bonding the laminate.

10. The method of claim 6, wherein the first region of the modified substrate differs from the second region of the modified substrate in at least one of the following properties: breathability, stiffness, strength, extensibility, caliper, z-directional resiliency, softness, and tear resistance.

* * * * *